(12) United States Patent
Concha et al.

(10) Patent No.: US 12,220,445 B2
(45) Date of Patent: Feb. 11, 2025

(54) INERT MATRICES FOR QUALITATIVE AND SEMI-QUANTITATIVE SEED AMPLIFICATION ASSAYS

(71) Applicant: Amprion, Inc., San Francisco, CA (US)

(72) Inventors: Luis Concha, San Diego, CA (US); Carly Farris, San Diego, CA (US); Yihua Ma, Corona, CA (US); Hieu Huu Nguyen, San Diego, CA (US)

(73) Assignee: Amprion, Inc., San Francisco, CA (US)

( * ) Notice: Subject to any disclaimer, the term of this patent is extended or adjusted under 35 U.S.C. 154(b) by 0 days.

(21) Appl. No.: 17/931,104

(22) Filed: Sep. 9, 2022

(65) Prior Publication Data

US 2023/0084155 A1    Mar. 16, 2023

Related U.S. Application Data

(63) Continuation-in-part of application No. PCT/US2021/021441, filed on Mar. 9, 2021.

(60) Provisional application No. 63/328,443, filed on Apr. 7, 2022, provisional application No. 63/243,470, filed on Sep. 13, 2021, provisional application No. 62/986,921, filed on Mar. 9, 2020.

(51) Int. Cl.

| | | |
|---|---|---|
| *A61K 39/00* | (2006.01) | |
| *A61K 31/185* | (2006.01) | |
| *A61K 38/17* | (2006.01) | |
| *A61K 38/38* | (2006.01) | |
| *A61K 39/395* | (2006.01) | |
| *A61P 1/00* | (2006.01) | |
| *A61P 1/04* | (2006.01) | |
| *A61P 25/00* | (2006.01) | |
| *A61P 25/02* | (2006.01) | |

(52) U.S. Cl.
CPC .......... *A61K 38/385* (2013.01); *A61K 31/185* (2013.01); *A61K 38/1774* (2013.01)

(58) Field of Classification Search
CPC .................. A61K 38/385; A61K 31/185
See application file for complete search history.

(56) References Cited

U.S. PATENT DOCUMENTS

| | | |
|---|---|---|
| 2005/0136542 A1 | 6/2005 | Todtleben et al. |
| 2006/0121534 A1 | 6/2006 | Rawson et al. |
| 2010/0210604 A1 | 8/2010 | Meythaler |
| 2013/0210141 A1 | 8/2013 | Rajesh et al. |
| 2013/0289022 A1 | 10/2013 | Ringe et al. |
| 2015/0025003 A1 | 1/2015 | Spetzler et al. |
| 2016/0077111 A1 | 3/2016 | Jara et al. |
| 2017/0224786 A1 | 8/2017 | Hunt |
| 2017/0247685 A1 | 8/2017 | Short |
| 2017/0349936 A1 * | 12/2017 | Daum ................ C12N 15/1003 |
| 2020/0056205 A1 | 2/2020 | Wilson et al. |
| 2021/0063416 A1 | 3/2021 | Concha et al. |

FOREIGN PATENT DOCUMENTS

| | | | |
|---|---|---|---|
| CN | 106916220 A * | 7/2017 | |
| WO | 2012025582 | 3/2012 | |
| WO | 2013097607 | 7/2013 | |
| WO | WO-2019193603 A1 * | 10/2019 | ............ C12N 5/061 |
| WO | WO-2020162752 A1 * | 8/2020 | ............ A61K 39/12 |
| WO | 2021183469 | 9/2021 | |

OTHER PUBLICATIONS

Rozga et al, "Human serum albumin coordinates Cu(II) at its N-terminal binding site with 1 pM affinity," J Biol Inorg Chem 12:913-918 (2007) (Year: 2007).*
English machine translation of CN106916220A, provided by USPTO (2017) (Year: 2017).*
Bio-Rad Laboratories, Inc, "Quick Start Bradford Protein Assay Instruction Manual," Sep. 25, 2007 (Sep. 25, 2007), pp. 1-36. Retrieved from the Internet: Retrieved from Internet: <https://www.bio-rad.com/webroot/web/pdf/lsr/literature/4110065A.pdf> on May 14, 2021 (May 14, 2021). entire document.
Stamou et al. "Fc Gamma Receptors are Expressed in the Developing Rat Brain and Activate Downstream Signaling Molecules Upon Cross-Linking with Immune Complex," Journal of Neuroinflammation, Jan. 6, 2018 (Jan. 6, 2018), vol. 15, No. 7, pp. 1-23. entire document.
International Search Report and Written Opinion issued in PCT/US2021/021441, mailing date Jun. 17, 2021.
International Preliminary Report on Patentability issued in PCT/US2021/021441, dated Sep. 6, 2022.
International Search Report and Written Opinion in PCT app. No. PCT/US22/76243 issued on Jan. 13, 2023.
International Preliminary Report on Patentability issued in PCT/US2022/076243 on Mar. 5, 2024.

* cited by examiner

*Primary Examiner* — Julie Ha
*Assistant Examiner* — Kristina M Hellman
(74) *Attorney, Agent, or Firm* — Kern Kendrick, LLC; Benjamen E. Kern; Charlemagne Kern

(57) ABSTRACT

Inert matrices for use with α-synuclein seed amplification assays (αS-SAAs) are provided. The inert matrices accurately reflect the absence of misfolded αS protein when used as a negative control, in the form of no, perceptively low, or delayed αS substrate self-aggregation, yet will readily permit aggregation of the αS substrate with seeds when used as a positive control. The inert matrices may be used to screen for αS-SAA reagent competence. The inert matrices may be used to dilute samples taken from peripheral biological matrices. Finally, the inert matrices may be used as a diluent for serial dilutions of αS-SAA samples, to enable semi-quantitative versions of αS-SAAs.

15 Claims, 18 Drawing Sheets
Specification includes a Sequence Listing.

| Assay | Fast Assay | | Fast Assay | | Fast Assay | | Alternative Fast Assay | |
|---|---|---|---|---|---|---|---|---|
| Substrate | AMP-A | | AMP50 | | AMP50 | | AMP48 | |
| Diluent | Neg-NPH CSF | | Neg-NPH CSF | | Synthetic CSF | | Synthetic CSF | |
| CSF ID# | 2603 | 2978 | 2603 | 2978 | 2603 | 2978 | 2603 | 2978 |
| Neat | ●●●● | ●●●○ | ●●●● | ●●●● | ●●●● | ●●●● | ●●●● | ●●●● |
| 1:3 | ●●●● | ●●○○ | ●●●● | ●●○○ | ●●●● | ●●●● | ●●●● | ●●●● |
| 1:9 | ●●●○ | ○●○○ | ●●●● | ●●○○ | ●●●● | ●●○○ | ●●●● | ●●●○ |
| 1:27 | ●●●● | ○○○○ | ●●●○ | ○○○○ | ●○○○ | ○○○○ | ●●●○ | ○○○○ |
| 1:81 | N/T | N/T | N/T | N/T | ○○○○ | ○○○○ | ●○○○ | ○○○○ |
| 1:243 | N/T | N/T | N/T | N/T | ○○○○ | ○○○○ | ○○○○ | ○○○○ |
| 1:729 | N/T | N/T | N/T | N/T | ○○○○ | ○○○○ | ○○○○ | ○○○○ |
| $SD_{50} \pm SE$ | 67.5±0.5 | 10.8±0.6 | 97.3±0.3 | 3.6±0.3 | 67.5±0.5 | 15.6±0.6 | 202.3±0.3 | 22.5±0.3 |

FIG. 14

SEQUENCE LISTING

```
Sequence total quantity: 2
SEQ ID NO: 1              moltype = AA   length = 140
FEATURE                   Location/Qualifiers
REGION                    1..140
                          note = Synthetic
source                    1..140
                          mol_type = protein
                          organism = synthetic construct
SEQUENCE: 1
MDVFMKGLSK AKEGVVAAAE KTKQGVAEAA GKTKEGVLYV GSKTKEGVVH GVATVAEKTK   60
EQVTNVGGAV VTGVTAVAQK TVEGAGSIAA ATGFVKKDQL GKNEEGAPQE GILEDMPVDP  120
DNEAYEMPSE EGYQDYEPEA                                              140

SEQ ID NO: 2              moltype = AA   length = 146
FEATURE                   Location/Qualifiers
REGION                    1..146
                          note = Synthetic
source                    1..146
                          mol_type = protein
                          organism = synthetic construct
SEQUENCE: 2
MDVFMKGLSK AKEGVVAAAE KTKQGVAEAA GKTKEGVLYV GSKTKEGVVH GVATVAEKTK   60
EQVTNVGGAV VTGVTAVAQK TVEGAGSIAA ATGFVKKDQL GKNEEGAPQE GILEDMPVDP  120
DNEAYEMPSE EGYQDYEPEA HHHHHH                                       146
```

INERT MATRICES FOR QUALITATIVE AND SEMI-QUANTITATIVE SEED AMPLIFICATION ASSAYS

CROSS-REFERENCE TO RELATED APPLICATIONS

This application is a continuation in part of International Application No. PCT/US2021/021441, filed on Mar. 9, 2021, which claims the benefit of U.S. Provisional Application No. 62/986,921, filed on Mar. 9, 2020. This application also claims the benefit of U.S. Provisional Application No. 63/243,470, filed on Sep. 13, 2021, and U.S. Provisional Application No. 63/328,443, filed on Apr. 7, 2022. Each of these applications is incorporated by reference herein in its entirety.

STATEMENT REGARDING FEDERALLY SPONSORED RESEARCH OR DEVELOPMENT

This invention was made with Government support under 1U44NS111672 awarded by the National Institute of Neurological Disorders and Stroke of the National Institutes of Health. The Government has certain rights in the invention.

SEQUENCE LISTING

A Sequence Listing has been submitted electronically in XML format and is hereby incorporated by reference in its entirety. The XML copy, created on Sep. 9, 2022, is named Amprion-sCSFQ_ST26.xml and is 3,705 bytes in size.

BACKGROUND

Seed Amplification Assays (SAAs) have provided a highly sensitive and specific means for detecting biomarker misfolded protein aggregates in tissues and fluids for titers that are too low for detection by traditional immunoassay methods. See Russo M J, Orru C D, Concha-Marambio L. et al. High diagnostic performance of independent alpha-synuclein seed amplification assays for detection of early Parkinson's disease [published correction appears in Acta Neuropathol Commun. 2021 Nov. 26; 9(1):190]. *Acta Veuropathol Commun.* 2021; 9(1):179. Published 2021 Nov. 6. doi:10.1186/s40478-021-01282-8, which is incorporated by reference herein in its entirety. SAAs allow for much earlier diagnosis of pathologies involving misfolded proteins, which may prove critical to treatment of the disease and prevention or mitigation of symptoms. See, e.g., Concha-Marambio L, Farris, Carly M, et al. Seed amplification assay to diagnose early Parkinson's and predict dopaminergic deficit progression. Movement Disorders. 2021; 36(10): 2444. Published 2021 Jul. 8. doi.org/10.1002/mds.2871, which is incorporated by reference herein in its entirety.

SAAs rely on the accelerated amplification of misfolded protein aggregates that are endogenous to a biological sample (seeds), at the expense of monomeric protein of the same type used as assay substrate, while avoiding self-aggregation of the latter. As a negative control, SAAs commonly use a biological sample from a known healthy control (HC) donor, since no reliable, commercially available synthetic control solution exists for this purpose. The negative control is subjected to the same conditions as the biological sample of interest, including intermittent shaking and addition of substrate, buffer, and a fluorescent probe. If the negative control shows no aggregation, and the biological sample shows no aggregation (that is, no amplification of the seeds), the patient is considered "negative," or aggregation is deemed "not detected." If the negative control shows no aggregation, and the biological sample shows aggregation, the patient is considered "positive," or aggregation is deemed "detected." If the negative control shows aggregation, the results must be discarded, and the assay must be repeated, as positivity in the negative control indicates a problem in the assay, either with handling, reagent stability, or quality of consumables. Thus, the negative control must not induce or permit self-aggregation of the substrate.

As a positive control, SAAs commonly use a biological sample from a patient with confirmed diagnosis of a relevant protein misfolding disorder, or a biological sample "spiked" with a known quantity of synthetic misfolded protein aggregates (synthetic seeds) of the same type as the biological biomarker. Again, human samples are used because no commercially available synthetic control solution exists that could sustain the amplification of synthetic seeds while suppressing self-aggregation of the substrate. The positive control is subjected to the same conditions as the biological sample. If the positive control shows aggregation, the assay conditions are compatible with seed amplification, which means reagents (including the substrate), consumables, and handling were of the necessary quality to detect the biomarker. If the positive control does not show aggregation, the results must be discarded, and the assay must be repeated, as lack of aggregation of the positive control indicates a problem in the assay, either with handling, reagent stability, or quality of consumables.

Recent studies show that cerebrospinal fluid (CSF) closely reflects brain matter as it respects the presence of misfolded protein. See, e.g., Shahnawaz, M., Mukherjee, A., Pritzkow, S. et al. Discriminating α-synuclein strains in Parkinson's disease and multiple system atrophy. *Nature* 578, 273-277 (2020). Thus, detection of misfolded protein in CSF is of particular importance. Unfortunately, compositions used as inert or neutral assay matrices for positive and negative controls in research contexts too frequently induce or permit self-aggregation of the substrate (in a negative control) or prevent aggregation in the presence of seeds, endogenous or synthetic (in a positive control).

Moreover, it is impossible to rely on human CSF from a healthy donor as a reproducible matrix for the clinical use of SAA for diagnostic purposes. First, CSF is a very complex biofluid that presents dramatic differences between individual donors. These differences are greater when comparing healthy versus diseased patients, but patients with similar health statuses can have very different CSF compositions. In some cases, CSF samples from healthy donors may induce self-aggregation, while in other cases, CSF samples from healthy donors may partially inhibit seeded aggregation. Additionally, as a practical matter, healthy human CSF samples are not available in unlimited supplies.

Thus, a need exists for an inert matrix for use as a control solution that can be used as-is, is readily available and in plentiful supplies, and will accurately reflect the absence of misfolded protein when used as a negative control, in the form of no, perceptively low, or delayed substrate self-aggregation, yet will readily permit aggregation of the substrate with seeds when used as a positive control.

While alpha-synuclein (αS)-SAA of CSF is the gold standard for detecting misfolded αS aggregates, obtaining CSF requires an invasive lumbar puncture, also known as a spinal tap, to remove a sample of CSF from the subarachnoid space in the spine. αS-SAAs of peripheral matrices (e.g., blood, saliva, skin, and olfactory mucosa) are known, see, e.g., U.S. Pat. Nos. 10,989,718, 11,079,396, and 11,099, 197, each of which is incorporated by reference herein in its entirety, but a reliable inert matrix for use as a diluent in the sample processing of such peripheral matrices is still needed. Cf. U.S. Provisional Application No. 63/375,126 filed on Sep. 9, 2022, which is incorporated by reference herein in its entirety.

As one of the most challenging aspects of SAAs is identifying competent substrate, that is, substrate that does not self-aggregate but does aggregate in the presence of seeds in biological sample milieu, a need also exists for an inert matrix for use as a control solution that may be used to screen for substrate competence (as well as the competence of other reagents and consumables used in the SAA).

Finally, quantification of the biomarker remains a challenge. Quantitative assays use standards to measure the concentration of a given analyte (in M or mg/mL). See, e.g., U.S. Pat. No. 10,215,763 and U.S. Patent Publication No. US20190137515A1 (the Prion References), each of which is incorporated by reference herein in its entirety. αS-SAAs are quantitative under ideal conditions (synthetic seeds in buffer), see, e.g., Shahnawaz, M. et al. Development of a Biochemical Diagnosis of Parkinson Disease by Detection of α-Synuclein Misfolded Aggregates in Cerebrospinal Fluid. *JAMA Neurol.* 74, 163 (2017); and Groveman, B. R. et al. Rapid and ultra-sensitive quantitation of disease-associated α-synuclein seeds in brain and cerebrospinal fluid by αSyn RT-QuIC. *Acta Neuropathol. Commun.* 6, 7 (2018), but quantification as described in the Prion References is infeasible in the context of αS-SAAs of biological samples for at least two reasons. First, no concentration standard exists with the same aggregation activity as endogenous αS aggregates; synthetic seeds aggregate much faster and would lead to gross underestimation of endogenous αS aggregates. In addition, a concentration standard should match the molecular weight distribution of the αS aggregates, as different species may have different seeding activity. Thus, synthetic seeds cannot be accurately used as absolute concentration standards. Second, biological fluids are complex matrices, and the kinetics of aggregation vary from patient to patient. For example, patients with the same concentration of αS in CSF could display different aggregation patterns due to a differential in their respective CSF matrices. Thus, a need exists for an inert matrix for use as a diluent for serial dilutions of SAA samples, to enable semi-quantitative versions of SAAs that estimate relative αS aggregate levels and allow comparison between biological samples to rank-order them.

SUMMARY

In one aspect, an inert matrix for use in an αS-SAA is provided. In one aspect, the inert matrix (sometimes hereafter referred to as a synthetic CSF or sCSF) comprises: (A) a plasma protein comprising either: (1) human serum albumin (HSA); or (2) is selected from the group consisting of bovine serum albumin (BSA), BSA precursor protein, transferrin, and Immunoglobulin G, and combinations thereof, and (B) an aqueous physiological salt solution comprising NaCl. Where the plasma protein comprises HSA, the sCSF may further comprise a detergent, e.g., sarkosyl, and a buffer composition, e.g., (4-(2-hydroxyethyl)-1-piperazineethanesulfonic acid) (HEPES). In one aspect, the HEPES maintains the pH of the HSA-comprising sCSF at about 7.5.

In one aspect, a method is provided for using the sCSF as a negative control in an αS-SAA, the method comprising: (I) providing an sCSF as disclosed herein; (II) providing a pre-incubation mixture, the pre-incubation mixture comprising: (A) a monomeric αS substrate; (B) a buffer composition; (C) a salt composition; (D) a fluorescent protein aggregation indicator; and, optionally, (E) a bead; (III) combining the sCSF and the pre-incubation mixture to form an incubation mixture; (IV) incubating the incubation mixture with intermittent agitation cycles to form an incubated mixture; (V) illuminating the incubated mixture with a wavelength of light sufficient to excite the fluorescent protein aggregation indicator if the fluorescent protein aggregation indicator is bound to a protein aggregate; (VI) determining a first fluorescence intensity; and (VII) comparing the first fluorescence intensity to a predetermined second fluorescence intensity, wherein a second fluorescence intensity that is greater than the first fluorescence intensity is indicative of the absence of perceptible amounts of self-aggregated αS substrate in the sCSF.

In one aspect, an sCSF is provided that is suitable for determining the competence of one or more of the reagents and consumables in an αS-SAA, including the competence of the αS monomeric protein as an αS-SAA substrate and/or the competence of the SAA buffer composition. In one aspect, as shown in FIG. 1 without a bead, the method comprises: (A) providing an incubation mixture, the incubation mixture comprising: (1) a monomeric αS protein; (2) a buffer composition; (3) a salt composition; (4) a fluorescent protein aggregation indicator; (5) sCSF as disclosed herein; and, optionally, (6) a bead; (B) incubating the incubation mixture with intermittent agitation cycles to form an incubated mixture; (C) illuminating the incubated mixture with a wavelength of light sufficient to excite the fluorescent protein aggregation indicator if the fluorescent protein aggregation indicator is bound to a protein aggregate; and (D) determining a fluorescence intensity during incubation, wherein the absence of a significant increase in fluorescence is indicative of the absence of self-aggregation of the monomeric αS protein, and wherein the absence of self-aggregation of the monomeric αS protein is indicative of the competence of the αS monomeric protein as an αS-SAA substrate and the competence of the buffer composition.

In one aspect, an sCSF is provided that is suitable for determining the competence of one or more of the reagents and consumables in an αS-SAA, including the competence of the αS monomeric protein as an αS-SAA substrate and/or the competence of the SAA buffer composition. In one aspect, as shown in FIG. 2 without a bead, the method comprises: (A) providing a recombinant synthetic αS seed in an sCSF as disclosed herein; (B) providing a pre-incubation mixture, the pre-incubation mixture comprising: (1) a monomeric αS protein; (2) a buffer composition; (3) a salt composition; (4) a fluorescent protein aggregation indicator; and, optionally, (5) a bead; (C) combining the recombinant synthetic αS seed and the pre-incubation mixture to form an incubated mixture; (D) incubating the incubation mixture with intermittent agitation cycles to form an incubated mixture; (E) illuminating the incubated mixture with a wavelength of light sufficient to excite the fluorescent protein aggregation indicator if the fluorescent protein aggregation indicator is bound to a protein aggregate; and (F) determining a fluorescence intensity during incubation, wherein a significant increase in fluorescence is indicative of amplification of the synthetic seeds at the expense of the monomeric αS protein, which is indicative of the competence of the αS monomeric protein as an αS-SAA substrate and the competence of the buffer composition.

In one aspect, an sCSF is provided that is suitable as a diluent in a semi-quantitative method for detecting the presence of misfolded αS aggregates. In one aspect, the method comprises: (A) providing: (1) a first human biological sample; and (2) a second human biological sample; (B) providing a pre-incubation mixture as described herein; (C) serially diluting: (1) the first biological sample by removing a portion of the first biological sample and combining the removed portion with a volume of an sCSF as disclosed herein to form a diluted first biological sample; and (2) the second biological sample by removing a portion of the second biological sample and combining the removed portion with a volume of the sCSF to form a diluted second biological sample; (D) repeating step (C) with successively diluted first biological samples and with successively diluted second biological samples a predetermined number of times; (E) subjecting each of the successively diluted first and second biological samples to an αS-SAA.

In another aspect, a semi-quantitative method for detecting the presence of misfolded αS aggregates in a plurality of human biological samples is provided, the method comprising: (A) providing: (1) a first human biological sample, divided between at least two reaction vessels to form individual first human biological sample aliquots; (2) providing a second human biological sample, divided between at least two reaction vessels to form individual second human biological sample aliquots; and (3) providing a third human biological sample, divided between at least two reaction vessels to form individual third human biological sample aliquots; (B) providing a pre-incubation mixture, the pre-incubation mixture comprising: (1) a monomeric αS protein; (2) a buffer composition; (3) a salt composition; and (4) an indicator comprising a fluorophore; (C) combining: (1) in one of the first plurality of reaction vessels, a first aliquot of the first biological sample and the pre-incubation mixture to form a first baseline incubation mixture; (2) in one of the second plurality of reaction vessels, a first aliquot of the second biological sample and the pre-incubation mixture to form a second baseline incubation mixture; and (3) in one of the third plurality of reaction vessels, a first aliquot of the third biological sample and the pre-incubation mixture to form a third baseline incubation mixture; (D) incubating the baseline incubation mixtures with intermittent agitation cycles to form baseline incubated mixtures; (E) illuminating the baseline incubated mixtures with a wavelength of light that excites the fluorophore; (F) determining a level of fluorescence during incubation, wherein an increase in the level of fluorescence indicates the presence of αS aggregates in the respective biological sample, and determining a time required for the level of fluorescence to reach half of the maximum fluorescence for the respective biological sample (Baseline $T_{50}$); and (G) normalizing the Baseline $T_{50}$ by: (1) adding to a second aliquot of the first biological sample a quantity of exogenous αS seeds to form a spiked first biological sample; (2) adding to a second aliquot of the second biological sample an equal quantity of exogenous αS seeds to form a spiked second biological sample; (3) adding to a second aliquot of the third biological sample an equal quantity of exogenous αS seeds to form a spiked third biological sample; (4) repeating steps (C)-(F) on the spiked biological samples; and (5) determining a normalized activity coefficient for each biological sample, y, according to the following equation: (a) φ (first biological sample)=Baseline $T_{50}$ (first biological sample)/Spiked $T_{50}$ (first biological sample); (b) φ (second biological sample)=Baseline $T_{50}$ (second biological sample)/Spiked $T_{50}$ (second biological sample); and (c) φ (third biological sample)=Baseline $T_{50}$ (third biological sample)/Spiked $T_{50}$ (third biological sample); and (H) comparing the normalized activity coefficient for each biological sample with a clinically deduced rating on a disease progression scale.

BRIEF DESCRIPTION OF THE FIGURES

The present invention may be more readily understood by reference to the following Figures, wherein:

FIG. 14 shows a chart comparing $SD_{50}$ values for two CSF samples in fast αS-SAA or alternative fast αS-SAA conditions in NPH-CSF or sCSF as the inert matrix.

DETAILED DESCRIPTION

Figure 1:
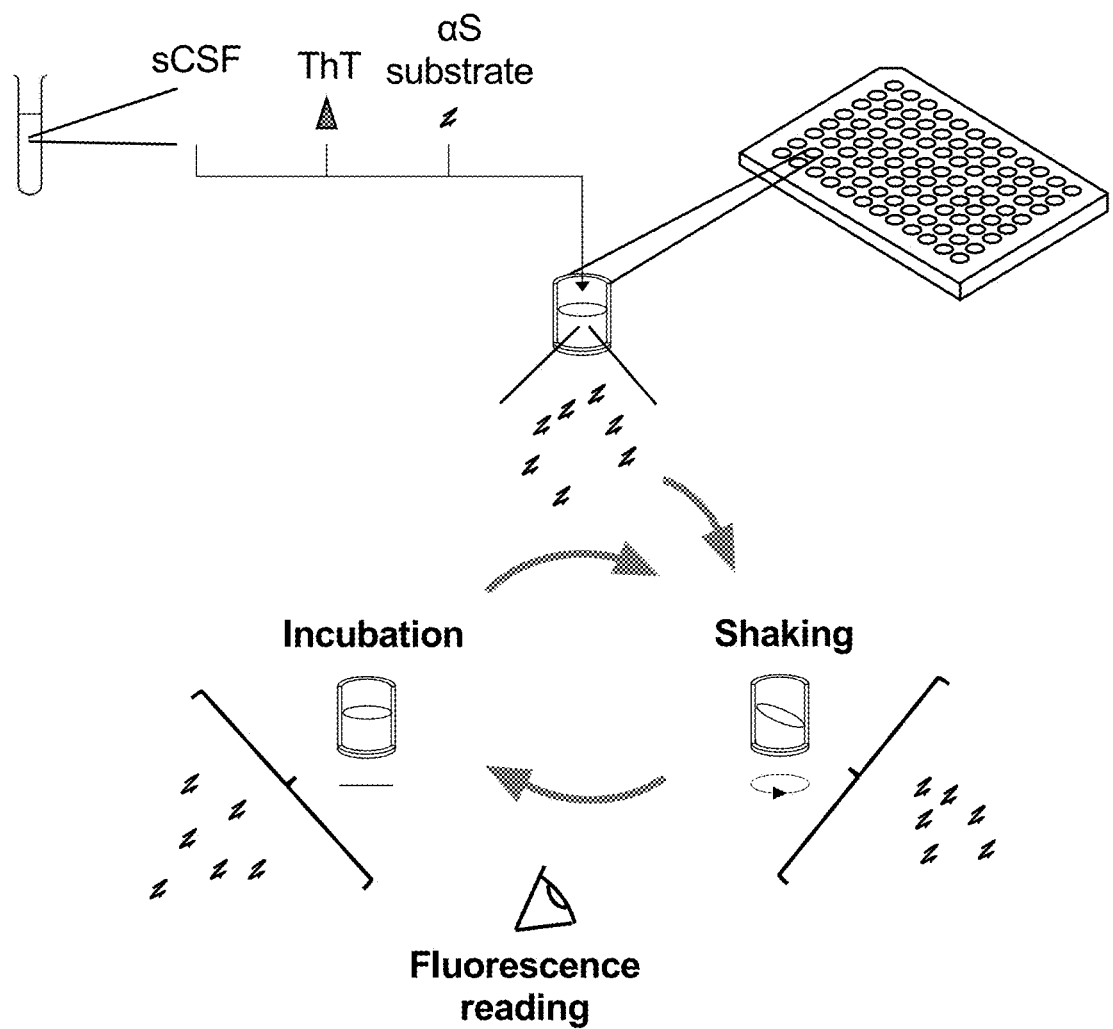
FIG. 1 is an example depiction of a "slow" (that is, without a bead) αS-SAA using an sCSF as a negative control and/or in the determination of the competency of a monomeric αS protein as an αS substrate (specifically, to determine whether the monomeric αS protein is prone to self-aggregate).
Figure 2:
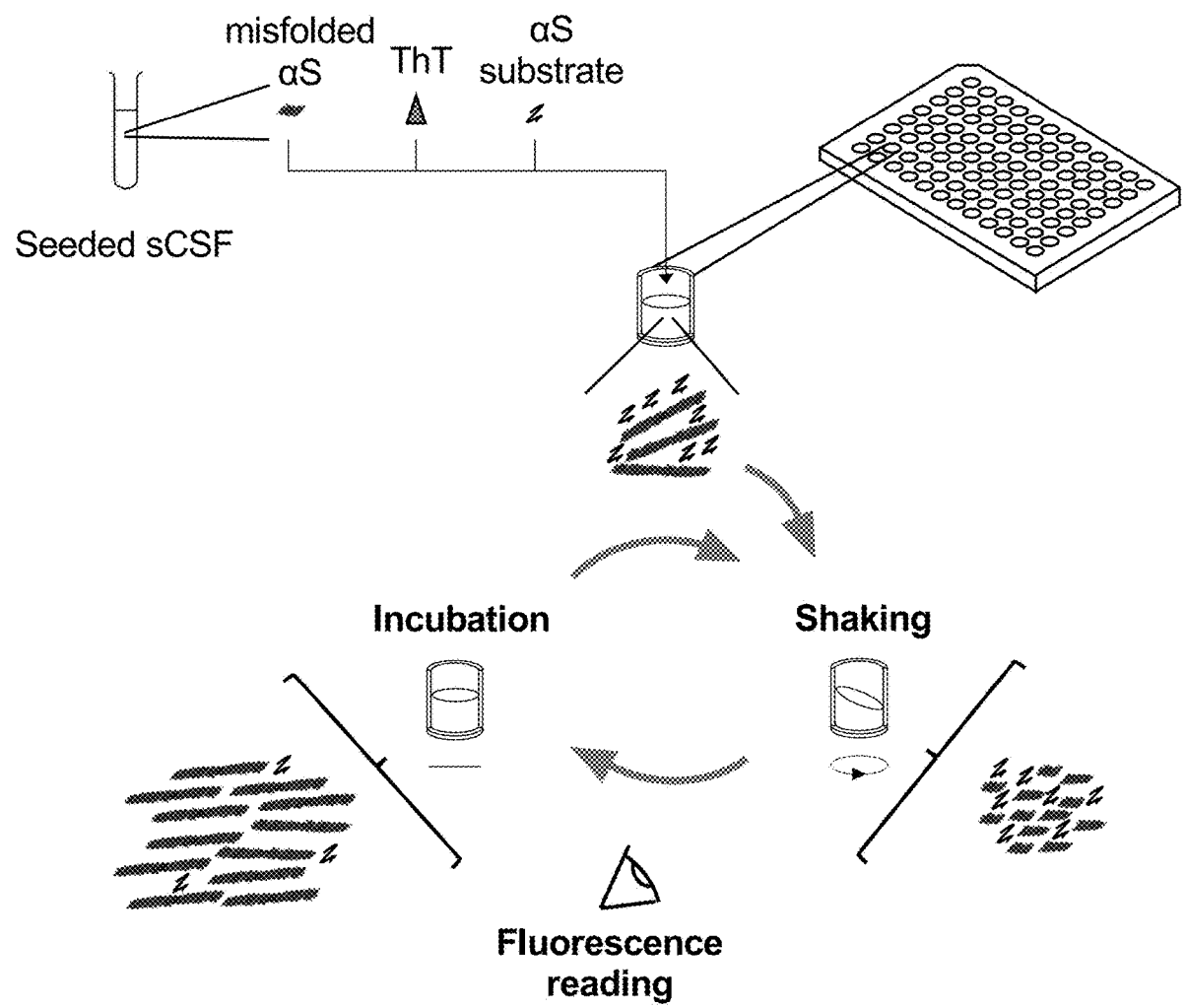
FIG. 2 is an example depiction of the slow αS-SAA using an sCSF that contains recombinant synthetic αS seeds in the determination of the competency of a monomeric αS protein as an αS substrate (specifically, to determine whether the monomeric αS protein can aggregate with αS seeds).

Inert matrices, or sCSFs, for αS SAA are provided. The sCSFs accurately reflect the absence of misfolded protein when used as a negative control, in the form of no, perceptively low, or delayed substrate self-aggregation, yet will readily permit aggregation of the substrate with seeds when used as a positive control. The sCSFs may be used to screen for substrate and other reagent competence. The cCSFs may be used as a diluent for pre-processing of peripheral matrices. Finally, the sCSFs may be used as a diluent for serial dilutions of SAA samples, to enable semi-quantitative versions of SAAs.

Definitions

The term "about" in conjunction with a number is intended to include ±10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about" or a clear indication of a range (e.g., ±10%) the exact number is intended. In other words, "10" means 10.

The singular forms "a," "an," and "the" include plural referents unless the context clearly dictates otherwise. Thus, for example, reference to "a bead" also includes a plurality of beads.

Where a range of values is provided, each intervening value, to the tenth of the unit of the lower limit unless the context clearly dictates otherwise, between the upper and lower limit of that range, and any other stated or intervening value in that stated range, is encompassed. The upper and lower limits of these smaller ranges may independently be included in the smaller ranges and are also encompassed, subject to any specifically excluded limit in the stated range. Where the stated range includes one or both of the limits, ranges excluding either or both of those included limits are also included.

"Misfolded αS aggregate" or "αS aggregate" refers to aggregates of misfolded αS protein. Aggregates may be referred to as oligomers or polymers, and aggregation may be referred to as oligomerization or polymerization.

A "misfolded αS protein" is an αS protein that lacks all or part of the structural conformation of the protein as it exists in its typical, nonpathogenic normal function within a biological system. A misfolded αS protein may aggregate. A misfolded αS protein may localize in a protein aggregate. A misfolded αS protein may be a non-functional protein. A misfolded αS protein may be a pathogenic conformer of the protein.

As used herein, "soluble" species, including soluble misfolded αS aggregate, may form a solution in biological fluids under physiological conditions, whereas "insoluble" species may be present as precipitates, fibrils, deposits, tangles, or other non-dissolved forms in such biological fluids. A species that dissolves in a non-biological fluid but not a biological fluid under physiological conditions is considered insoluble. For example, fibrils of αS and the like may be dissolved in a solution of, e.g., a surfactant such as sodium dodecyl sulfate (SDS) in water but may still be insoluble in biological fluids under physiological conditions and are, therefore, considered insoluble.

Nucleation-dependent aggregation may be characterized by a slow "lag phase," wherein aggregated nuclei form and stimulate the rapid formation of further and/or larger aggregates. The lag phase may be minimized or eliminated by addition of pre-formed "nuclei" or "seeds." "Seeds" or "nuclei" refer to misfolded αS protein or short fragmented fibrils with the ability to induce further aggregation.

Aggregates of misfolded αS protein may be "de-aggregated," i.e., broken up or disrupted, to release smaller fragments and aggregates, e.g., fragmented fibrils and smaller misfolded αS aggregates. The catalytic activity of a collection of misfolded αS aggregate seeds may scale, at least in part with the number of seeds in a mixture. Accordingly, disruption of misfolded αS aggregates to release smaller misfolded αS aggregates and fragmented fibrils as seeds may lead to an increase in catalytic activity for further aggregation.

The phrases "monomeric αS protein" and "monomeric αS substrate" are used interchangeably and refer to one or more seed-free, αS protein molecules in their native, non-pathogenic configuration without the catalytic activity for aggregation associated with seeds.

When reference is made to the term "each," it is not meant to mean "each and every, without exception." For example, if reference is made to an incubation cycle, and "each incubation cycle" is said to involve certain steps, if the incubation cycle is conducted 10 times, and one of the incubation cycles involves the certain steps, then that incubation cycle is intended to meet the limitation.

The transitional phrase "consisting essentially of" limits the scope of a claim to the specified materials or steps "and those that do not materially affect the basic and novel characteristic(s)" of the claimed invention. MPEP § 2111.03 (III.).

Unless defined otherwise, all technical and scientific terms have the same meaning as commonly understood by one of ordinary skill in the art to which this invention belongs.

sCSFs

In one aspect, the sCSFs may comprise an aqueous physiological salt solution and a plasma protein.

The aqueous physiological salt solution may be designed to mimic physiological CSF. The aqueous physiological salt solution may comprise a water-based solution comprising a salt that corresponds to at least one of the salts that are present in human CSF. In some aspects, the aqueous physiological salt solution comprises one or more of sodium, potassium, chloride, calcium, magnesium, and phosphate ions. The salts in the aqueous physiological salt solution may be provided in concentrations similar to those found in human CSF. For example, an aqueous physiological salt solution may comprise 130-160 mM NaCl; 2.7-3.9 mM KCl; 1-10 mM $CaCl_2 \cdot 2H_2O$; 0.5-10 mM $MgCl_2 \cdot 6H_2O$; 0.5-5 mM $Na_2HPO_4 \cdot 7H_2O$; and 0.1-2 mM $NaH_2PO_4 \cdot H_2O$. In some aspects, the aqueous physiological salt solution is comprised of 148 mM NaCl; 3 mM KCl; 1.4 mM CaCl$_2$·2H$_2$O; 0.8 mM MgCl$_2$·6H$_2$O; 0.8 mM Na$_2$HPO$_4$·7H$_2$O; and 0.2 mM NaH$_2$PO$_4$·H$_2$O. For example, one aqueous physiological salt solution comprises about 150 mM Na, about 3 mM K, about 1.4 mM Ca, about 0.8 mM Mg, about 1.0 mM P, and about 155 mM Cl. In some aspects, the sCSF further comprises 20-25 mM sodium carbonate and/or 0.2-1.5 mM glucose or sucrose. In some aspects, the sCSF further comprises 0.2 to 1.0 mg/mL sucrose. In some aspects, the physiological salt solution is optional. In some aspects, the physiological salt solution consists essentially of an NaCl solution having a concentration of up to about 150 mM NaCl, including up to about (that is, within ±10% of) 75 mM NaCl.

Methods for preparing aqueous physiological salt solutions are known in the art, and components of aqueous physiological salt solutions are also commercially available. For example, in some aspects, the aqueous physiological salt solution comprises Harvard Apparatus artificial CSF, which is commercially available from Harvard Apparatus, Holliston, Massachusetts. In some aspects, the aqueous physiological salt solution comprises perfusion fluid, which is commercially available from M Dialysis Inc. In some independent aspects, Harvard Apparatus artificial and/or perfusion fluid are specifically excluded from use in this invention.

In some aspects, the sCSF may be a buffered solution. In one aspect, the buffer comprises HEPES. In some aspects, the buffer comprises between 1 mM HEPES and 1 M HEPES, including about 50 mM HEPES, about 100 mM HEPES, about 150 mM HEPES, about 200 mM HEPES, about 250 mM HEPES, about 500 mM HEPES, about 1M HEPES, or any value or range between any two of those concentrations.

The sCSF may have a pH that is lower than about 8, about 7.5, from about 5 to 8, from about 5.5 to about 7.5, from about 6 to about 7.5, from about 6 to about 7, about 6.5, or any value or range between any two of those pH values.

In one aspect, the sCSF is a buffered solution, the buffer comprises HEPES, and the pH is about 7.5.

The sCSF also comprises one or more plasma proteins. Plasma proteins are proteins normally found in blood plasma. Human CSF contains some of the proteins found in blood plasma, although in much lower concentrations. Human CSF contains approximately 0.3% plasma proteins or approximately 15 to 40 mg/dL of total plasma protein. Accordingly, in some aspects, the total plasma protein, which represents the combined amount of various plasma proteins in the solution, has a concentration ranging from 0.01 mg/mL to 15 mg/mL.

Examples of plasma proteins comprise albumins (e.g., HSA and BSA), fibrinogen, albumin precursor protein (e.g., BSA precursor protein), transthyretin, gamma globulins (e.g., immunoglobulin G), apolipoproteins (ApoAl, ApoE, ApoJ, ApoD, etc.), lipoproteins (e.g., high density or low density lipoprotein), complement proteins, prothrombin, and transferrin. In some aspects, the plasma protein is selected from the group consisting of HSA, BSA, BSA precursor protein, transferrin, and Immunoglobulin G, and combinations thereof.

In some aspects, the plasma protein consists of or consists essentially of 0.1 to 0.3 mg/mL BSA. In other aspects, the plasma protein consists of or consists essentially of 0.1 to 0.2 mg/mL BSA and 0.02 to 0.06 mg/mL transferrin. In a further aspect, the plasma protein consists of or consists essentially of 0.4 to 0.5 mg/mL BSA, 0.01 to 0.03 mg/mL BSA precursor protein, and 0.005 to 0.02 mg/mL Immunoglobulin G, and the sCSF also comprises 0.2 to 1.0 mg/mL sucrose.

In some aspects, the plasma protein consists of or consists essentially of HSA in a concentration of 0.01 mg/mL to 15 mg/mL, including 0.01 mg/mL to 1.5 mg/mL, from 0.02 mg/mL to 0.8 mg/mL, from 0.02 mg/mL to 0.4 mg/mL, from 0.05 mg/mL to 0.4 mg/mL, about 1.5 mg/mL, about 2.0 mg/mL, about 2.5 mg/mL, about 3.0 mg/mL, about 3.5 mg/mL, about 4.0 mg/mL, about 4.5 mg/mL, about 5.0 mg/mL, about 5.5 mg/mL, about 6.0 mg/mL, about 6.5 mg/mL, about 7.0 mg/mL, about 7.5 mg/mL, about 8.0 mg/mL, about 8.5 mg/mL, about 9.0 mg/mL, about 9.5 mg/mL, about 10.0 mg/mL, about 10.5 mg/mL, about 11.0 mg/mL, about 11.5 mg/mL, about 12.0 mg/mL, about 12.5 mg/mL, about 13.0 mg/mL, about 13.5 mg/mL, about 14.0 mg/mL, about 14.5 mg/mL, about 15.0 mg/mL, or any value or range between any two of those concentrations.

In some aspects, the sCSF comprises a detergent or a surfactant. In one aspect, the detergent is sodium lauroyl sarcosinate, also known as sarkosyl. In one aspect, the detergent is sodium dodecyl sulfate. In one aspect, the detergent is about 0.1% sarkosyl, about 0.2% sarkosyl, about 0.3% sarkosyl, about 0.4% sarkosyl, about 0.5% sarkosyl, about 0.6% sarkosyl, about 0.7% sarkosyl, about 0.8% sarkosyl, about 0.9% sarkosyl, about 1.0% sarkosyl, or any value or range between any two of those concentrations.

In one aspect, and particularly when acting as a control solution for the slow αS-SAA, such as disclosed in U.S. Pat. No. 10,989,718, which is incorporated by reference herein in its entirety, the sCSF consists essentially of Harvard Apparatus artificial CSF, 0.155 mg/mL BSA, and 0.042 mg/mL transferrin. About 0.155 mg/mL BSA is considered to be the physiological concentration of BSA in human CSF (or 1×). About 0.042 mg/mL transferrin is considered to be three times (3×) the physiological concentration of transferrin in human CSF. In another aspect, the sCSF consists essentially of Harvard Apparatus artificial CSF and 0.2015 mg/mL BSA (or 1.3× the physiological concentration of BSA in human CSF).

In some aspects, and particularly when acting as a control solution for the fast αS-SAA, such as disclosed in U.S. Pat. No. 11,079,396 and U.S. Provisional Application No. 63/375,126, each of which is incorporated by reference herein in its entirety, the sCSF may consist essentially of HEPES, HSA, and NaCl solution (in those aspects of U.S. Pat. No. 11,079,396 and U.S. Provisional Application No. 63/375,126 wherein the assay includes sarkosyl). In one aspect, wherein the assay does not include sarkosyl, the sCSF consists essentially of HEPES, NaCl solution, HSA, and sarkosyl. In one aspect, the sCSF consists essentially of 100 mM HEPES, pH 7.5, 75 mM NaCl, HSA, and 0.5% sarkosyl.

In some aspects, the sCSF is used as a component of a positive control. A positive control can be used to generate the result expected when αS aggregate is present in the biological sample (i.e., a positive result). The positive control further comprises a seed, whether endogenous or synthetic. In some aspects, the sCSF is a component of a negative control. A negative control can be used to generate the result expected when αS aggregate is not present in the biological sample (i.e., a negative result). The negative control further comprises a monomeric αS substrate and all of the components of the pre-incubation mixture. In further aspects, the sCSF is a comparative control, which comprises a known amount of seed. A comparative control may be used as a benchmark for determining the amount of αS aggregate that has been formed using αS-SAA. In further aspects, the sCSF may be used as a diluent in a semi-quantitative αS-SAA.

In one aspect, the sCSF may contain multiple system atrophy (MSA) or PD or Lewy Body Dementia (LBD) synthetic seeds as a disease-specific positive control, with results being used to compare and determine whether a human sample is from an MSA patient, a PD patient, an LBD patient, or a patient exhibiting more than one of these pathologies.

In another aspect, synthetic seeds may be used to create a calibration curve in the sCSF. The kinetic parameters of such a curve may help to determine the concentration of endogenous seeds in a biological sample.

In yet another aspect, the sCSF may be used a diluent in SAA of tissue such as skin or olfactory mucosa. Certain tissues may interfere with SAAs. When the seed concentration is high in the tissue, the sCSF may be used to dilute out the interfering aspects of the tissue, but still retain sufficient seeds in the SAA to undergo detectable amplification.

Biological Samples

A "biological sample" is meant to include any biological sample from a subject that is suitable for analysis for detection of misfolded αS aggregates. Suitable biological samples may include, for example, fluids or fluids expressed from amniotic fluid, bile, blood, blood plasma, CSF, cerumen, skin, exudate, feces, gastric fluid, lymph, milk, mucus, mucosal membrane, e.g., nasal mucosal membrane, including olfactory mucosa, peritoneal fluid, pleural fluid, pus, saliva, sebum, semen, sweat, synovial fluid, tears, and urine. When a biological fluid has been removed from the body and, as applicable, processed and/or prepared for use in the methods and kits described herein, it is referred to as a "biological sample" or, simply as a "sample." When a sample is referred to in the claims as being "provided," e.g., a CSF sample, a skin sample, an olfactory mucosal sample, a blood or blood plasma sample, or a saliva sample, the meaning that is intended is that the sample is provided in a processed and/or prepared form ready for SAA, unless the context dictates clearly otherwise. The methods and kits described herein are conducted and used in vitro.

As used herein, "αS" may refer to full-length, 140 amino acid alpha-synuclein protein, e.g., "αS-140." Other isoforms or fragments may include "αS-126," alpha-synuclein-126, which lacks residues 41-54, e.g., due to loss of exon 3; and "αS-112" alpha-synuclein-112, which lacks residue 103-130, e.g., due to loss of exon 5.

In one aspect, the monomeric αS substrate comprises, consists essentially of, or consists of wild type or recombinant human αS protein having 140 amino acids, having a molecular mass of 14,460 Da, and being represented by the sequence:

```
SEQ ID NO. 1:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

In some aspects, the monomeric αS substrate comprises, consists essentially of, or consists of a conservative variant of SEQ ID NO. 1. A conservative variant may be a peptide or amino acid sequence that deviates from SEQ ID NO. 1 only in the substitution of one or several amino acids for amino acids having similar biochemical properties and having a minimal or beneficial impact on the activity of the resultant protein in the αS-SAA. A conservative variant must functionally perform substantially like the base component, i.e., SEQ ID NO. 1. For example, a conservative variant of SEQ ID NO. 1 will aggregate with misfolded αS protein and will form aggregates with substantially similar reaction kinetics under similar reaction conditions. The conservative variant may have for example, one, two, three, four, five, six, seven (5%), and up to 14 (10%) substitutions in the amino acid sequence.

In some aspects, the monomeric αS substrate comprises a recombinant αS protein comprising six additional histidine amino acids (i.e., a polyHis purification tag) on the C-terminus of SEQ ID NO. 1, resulting in a molecular mass of 15,283 Da and being represented by the sequence:

```
SEQ ID NO. 2:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA HHHHHH
```

In some aspects, the monomeric αS substrate may be any of the monomeric αS substrates disclosed in U.S. Pat. No. 11,079,396 and conservative variants thereof. In some aspects, the monomeric αS substrate or conservative variant thereof specifically excludes a monomeric αS substrate consisting of SEQ ID NO: 1.

In some aspects, the monomeric αS substrate may be expressed and prepared as described in Shahnawaz, M. et al. Development of a Biochemical Diagnosis of Parkinson's Disease by Detection of alpha-Synuclein Misfolded Aggregates in Cerebrospinal Fluid. JAMA Neurol 74, 163-172 (2017), which is incorporated by reference herein in its entirety.

In some aspects, the monomeric αS substrate may be expressed and prepared as described in U.S. Pat. No. 11,254,718, which is incorporated by reference herein in its entirety.

In some aspects, the method may include providing the monomeric αS substrate in labeled form. A labeled monomeric αS substrate may be considered a conservative variant. The monomeric αS substrate in labeled form may include one or more of: a covalently incorporated radioactive amino acid, a covalently incorporated, isotopically labeled amino acid, a covalently incorporated fluorophore, and the like. Thus, detection of the misfolded αS aggregate may include detecting the monomeric αS substrate in labeled form as incorporated into the amplified portion of misfolded αS aggregate.

The pre-incubation mixture may include various concentrations of the monomeric αS substrate as a function of the total volume of the pre-incubation mixture prior to conducting an incubation cycle. In some aspects, the pre-incubation mixture may include the monomeric αS substrate in a concentration, or in a concentration range, of: between about 500 nM and about 500 µM; between about 1 µM and about 200 µM; between about 5 µM to about 100 µM; between about 10 µM and about 50 µM; between about 50 µM and about 75 µM; about 65 µM (i.e., about 1 mg/ml); 65 µM; between about 10 µM and about 30 µM; greater than 10 µM and less than 30 µM; about 20 µM; about 19.6 µM (i.e., about 0.3 mg/ml); or 19.6 µM. In one aspect, the pre-incubation mixture includes a concentration of the monomeric αS substrate as a function of the total volume of the pre-incubation mixture prior to conducting an incubation cycle of about 0.3 mg/ml.

Buffer Compositions

The pre-incubation mixture may include various buffer compositions. The buffer composition may be effective to maintain the pH of the reaction mixture in a range from about pH 5 to about pH 9, from about pH 6 to about pH 8, from about pH 6 to about pH 7, from about pH 7 to about pH 8, about pH 7, about pH 7.4, from about pH 6.2 to about pH 6.5, including pH 6.3, 6.4, and 6.5. In one aspect, the buffer composition may be effective to maintain the pH of the reaction mixture at about 6.5. In some aspects, the pre-incubation mixture comprises one or more of the buffers Tris-HCL, MES, PIPES, MOPS, BES, TES, and HEPES. In some aspects, the buffer comprises PIPES in a concentration of about 100 mM, about 200 mM, about 300 mM, about 400 mM, about 500 mM, about 600 mM, or about 700 mM. In one aspect, the buffer comprises PIPES in a concentration of about 100 mM.

Salt Solutions

In some aspects, the pre-incubation mixture comprises salt in a given concentration. The salt may, for example, enhance signal to noise ratio in fluorescence detection. In one aspect, the salt comprises NaCl. Other suitable salts may include KCl. In one aspect, the salt, e.g., NaCl, may be present in the pre-incubation mixture in a concentration of about 50 mM to about 1,000 mM, about 50 mM to about 500 mM, about 50 to about 150 mM, about 150 mM to about 500 mM, about 50 mM, about 150 mM, about 300 mM, about 500 mM, about 600 mM, or about 700 mM. In one aspect, the salt, e.g., NaCl, is present in a concentration of about 500 mM.

Indicators

In some aspects, pre-incubation mixture comprises an indicator to determine if a detectable amount of misfolded αS aggregate is present in the reaction mixture. The indicator can be characterized by exhibiting an indicating state in the presence of a detectable amount of misfolded αS aggregate and a non-indicating state in the absence of a detectable amount of misfolded αS aggregate. Determining the presence of misfolded αS aggregate in a biological sample may include detecting the indicating state of the indicator of misfolded αS aggregate. The indicating state of the indicator and the non-indicating state of the indicator may be characterized by a difference in fluorescence. Thus, the step of determining the presence of misfolded αS aggregate in a biological sample may include detecting the difference in fluorescence. In some aspects, a molar excess of the indicator may be used, the molar excess being, for example, greater than a total molar amount of the monomeric αS substrate and the misfolded αS aggregate in the reaction mixture.

In some aspects, the indicator comprises a fluorophore. In some aspects, the indicator may include one or more of. Thioflavin-T (ThT), Congo Red, m-I-Stilbene, Chrysamine G, PIB, BF-227, X-34, TZDM, FDDNP, IMPY, NIAD-4, luminescent conjugated polythiophenes, a fusion with a fluorescent protein such as green fluorescent protein and yellow fluorescent protein, derivatives thereof, and the like. A suitable indicator is ThT. In one aspect, wherein the indicator comprises ThT, the ThT concentration in the pre-incubation mixture is between about 5 μM and about 10 μM. In one aspect, wherein the indicator comprises ThT, the ThT concentration in the pre-incubation mixture is 10 μM.

Sarkosyl

In some aspects, the pre-incubation mixture comprises sarkosyl. In some aspects, the sarkosyl is present in a concentration of 0.01% w/v to about 1.0% w/v. In some aspects, the sarkosyl is present in a concentration of 0.05% w/v to about 0.2% w/v. In some aspects, the sarkosyl is present in a concentration of about 0.1% w/v.

Incubation Conditions

The reaction mixture may be held within a suitably sized container, such as a multi-well plate having a plurality of wells. For example, the multi-well plate may include 96 wells. The wells of the multi-well plate may have a volume of from 100 μL to 1000 μL, from 150 μL to 750 μL, or from 200 μL to 350 μL. In some aspects, at least one well of the multi-well plate contains one or more beads.

The temperature of the reaction mixture, in each incubation cycle, at a temperature in ° C., can independently be about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or a range between any two of the preceding values, for example, between about 15° C. and about 50° C., or between about 25° C. and about 45° C., or between about 30° C. and about 42° C. In some aspects, the incubation is carried out at about normal physiological temperatures for a warm-blooded animal. In further aspects, incubating the reaction mixture is conducted at a temperature between about 35° C. and about 45° C. or between about 37° C. and about 42° C. In one aspect, the method comprises incubating the reaction mixture at a temperature of about 42° C.

In several aspects, de-aggregating the incubation mixture may include subjecting the incubation mixture to physical disruption, such as shaking, sonication, stirring, freezing/thawing, laser irradiation, autoclave incubation, high pressure, homogenization, and the like. Shaking may include cyclic agitation, such as orbital agitation. The cyclic agitation may be conducted between about 50 rotations per minute (RPM) and 10,000 RPM. The cyclic agitation may be conducted between about 200 RPM and about 2000 RPM. The cyclic agitation may be conducted at about 500 RPM or about 600-800 RPM. In one aspect, the shaking comprises orbital agitation at about 800 RPM. De-aggregation of the incubation mixture may be conducted after each incubation cycle for between about 5 seconds and about 10 minutes, between about 30 seconds and about 1 minute, between about 45 seconds and about 1 minute, for about 1 minute, and the like.

The steps of incubating and de-aggregating the reaction mixture are repeated as necessary to amplify the misfolded αS aggregate of the biological sample to provide a detectable amount of misfolded α-S aggregate. Incubating the reaction mixture and de-aggregating the reaction mixture constitute an incubation cycle. The incubation cycle may be repeated between once and about 1000 times, between two times and about 500 times, between about 50 times and about 500 times, between about 150 times and about 250 times, and the like. In one aspect, for the final round of the incubation cycle, it may be advantageous to omit the de-aggregation step before performing the detecting step.

An incubation cycle may be carried out for a time between about 1 minute and about 5 hours, between about 10 minutes and about 2 hours, between about 15 minutes and about 1 hour, between about 25 minutes and about 45 minutes, and the like. In some aspects, incubating the reaction mixture and de-aggregating at least a portion of the misfolded αS aggregate includes an incubation cycle lasting from about 0.1 to 1 hours. Each incubation cycle may include independently incubating and de-aggregating the reaction mixture for one or more of: incubating between about 1 minute and about 5 hours and de-aggregating between about 5 seconds and about 10 minutes; incubating between about 10 minutes and about 2 hours and de-aggregating between about 30 sec and about 1 minute; incubating between about 14 minutes and about 1 hour and de-aggregating between about 45 seconds and about 1 minute; incubating between about 25 minutes and about 45 minutes and de-aggregating between about 45 seconds and about 1 minute; and incubating about 1 minute and de-aggregating about 1 minute. In one aspect, each incubation cycle includes incubating for about 14 minutes and de-aggregating for about 1 minute.

Beads

In some aspects, the pre-incubation mixture may include one or more beads. Beads are small, typically spherical objects such as high-density beads having a low friction surface that are commonly used as bearing beads. Including beads in the reaction mixture increases the rate of formation of misfolded αS aggregate from the monomeric αS substrate and the soluble, misfolded αS protein of the biological sample. These beads are different in composition and function from the antibody coated magnetic or paramagnetic beads or particles (e.g., Dynabeads) used in concentration and/or immune depletion steps as described elsewhere herein.

The beads may be comprised of a variety of chemically inert materials. For example, in some aspects, the beads are comprised of silica, glass, borosilicate glass, or $Si_3N_4$.

In some aspects, the beads comprise, consist essentially of, or consist of $Si_3N_4$. In some aspects, the beads comprise, consist essentially of, or consist of borosilicate glass. In one aspect, zirconium/silica beads are excluded. In one aspect, glass beads other than borosilicate glass beads are excluded.

In some aspects, the beads included in the incubation mixture may have a mean diameter of greater than 0.5 mm. In some aspects, the beads have a mean diameter from greater than 0.5 to about 10 mm. In some aspects, the beads have a mean diameter from greater than 0.5 mm to about 5 mm. In further aspects, the beads have a mean diameter ranging from greater than 0.5 mm to about 3.5 mm. In some aspects, the beads have a mean diameter from about 1.0 to about 10 mm, while in additional aspects the beads have a mean diameter from about 1.0 mm to about 5 mm. In further aspects, the beads have a mean diameter ranging from greater than 1.0 mm to about 3.5 mm. In some aspects, the beads have a mean diameter from 2.38 mm to about 10 mm, while in additional aspects the beads have a mean diameter from 2.38 mm to about 5 mm. In further aspects, the beads have a mean diameter ranging from greater than or equal to about 2.3 mm to about 3.5 mm, from about 2.38 to about 3.5 mm, or from about 2.45 mm to about 3.5 mm. In further aspects, the beads may have a mean diameter from about 1 mm to about 5 mm, from greater than 2.3 mm to about 5 mm, from greater than 3 mm to about 5 mm, about 2.38 mm, about 2.45 mm, or about 3.175 mm. In some aspects, the beads comprise, consist essentially of, or consist of $Si_3N_4$, have a mean diameter of 2.38 mm, and are blocked with bovine serum albumin (BSA). In some aspects, the beads comprise, consist essentially of, or consist of $Si_3N_4$, have a mean diameter of 3.175 mm, and are unblocked. In some aspects, the beads comprise, consist essentially of, or consist of borosilicate glass, have a mean diameter of 2.45 mm, and are unblocked. In some aspects, beads having a mean diameter of 2.3 mm or less are excluded from the invention. In some aspects, glass beads having a mean diameter of 2.3 mm or less are excluded from the invention. In some aspects, beads having a mean diameter of 3 mm or less are excluded from the invention. The size distribution of the beads is defined so that more than 90% of the beads are found between 80-120% of the mean bead diameter or between 90-110% of the mean bead diameter.

The number of beads included in the pre-incubation mixture can vary. In some aspects, the pre-incubation mixture consists of one bead. In some aspects, the pre-incubation mixture consists of two beads. In some aspects, the pre-incubation mixture comprises a plurality of beads. In one aspect, the pre-incubation mixture consists of two unblocked ⅛" (3.175 mm) $Si_3N_4$ beads.

In some aspects, the surface of the one or more beads is "blocked" with a protein. Blocking the surface of the bead with a protein refers to providing a coating or layer over all or a substantial portion of the surface of the bead. Any suitable biocompatible protein can be used to coat the surface of the bead. A suitable protein for use in blocking the surface of the bead is an albumin, such as BSA. Other suitable blocking proteins may include casein or milk powder. The one or more beads can be blocked by soaking the one or more beads in a solution including the protein. The solution can be a water solution and/or a buffered solution such as PIPES, Tris-HCl, MES, MOPS, BES, TES, and HEPES.

The incubation mixture is held within a suitably sized container, such as a test tube. Suitable sterile incubation containers are known to those skilled in the art. In some aspects, the incubation mixture is contained in a multi-well plate including a plurality of wells. For example, the multi-well plate can include 96 wells. In one aspect, such as when the beads are $Si_3N_4$ beads, the container may be a black bottom 96-well plate (Costar 3916). In one aspect, such as when the beads are $Si_3N_4$ beads, the container may be a bottom-read Greiner CBP plate. In one aspect, such as when the beads are borosilicate glass beads, the container may be a clear bottom 96-well plate (Costar 3603).

Detection

Detection includes repeating the steps of incubating and de-aggregating the reaction mixture as necessary to amplify sufficient misfolded αS aggregate present in the biological sample to provide an amplified incubation mixture having a detectable amount of misfolded αS aggregate. The incubation mixture may be contacted with an indicator, and the level of fluorescence of the amplified reaction mixture may be determined.

A suitable indicator is ThT, which is also known as Basic yellow 1. When ThT is added to samples containing β-sheet-rich deposits, such as the cross-β-sheet quaternary structure of amyloid fibrils, ThT fluoresces strongly with excitation and emission maxima at about 435 nm (or about 440 nm, depending on the fluorometer or spectrofluorometer) and about 485 nm (or about 490 nm, depending on the fluorometer or spectrofluorometer), respectively.

ThT fluorescence is typically measured by fluorescence spectroscopy using a filter fluorometer or spectrofluorometer. In some aspects, the ThT fluorescence emission intensity may be compared to the level of a corresponding control sample when carrying out the analysis to quantify the amount of misfolded αS aggregate in the biological sample. Once the ThT fluorescence level has been determined, it can be displayed in a variety of ways. For example, the levels can be displayed graphically on a display as numeric values, proportional bars (i.e., a bar graph), or any other display method known to those skilled in the art.

An increase in the level of fluorescence indicates the presence of αS aggregate in the biological sample. In some aspects, a significant increase in the level of fluorescence indicates the presence of αS aggregate in the biological sample. In some aspects, a "significant increase" is an increase in the level of fluorescence of the incubated mixture at maximum fluorescence of at least two times the standard deviation of the fluorescence of the incubated mixture at maximum fluorescence compared to the level of fluorescence of the incubated mixture at any point during the lag phase indicates the presence of αS aggregate in the biological sample.

Neurological Disorders and Synucleinopathies

αS aggregation may be associated with protein misfolding disorders (PMDs), e.g., PD, LBD, and MSA. However, existing technology is not clear whether this aggregation phenomenon is the cause of these diseases; it is only speculated that these misfolded αS aggregates may cause cell dysfunction and tissue damage, among other effects. That is to say, the methods and kits described herein do not directly determine whether an individual has a certain disease based on whether the individual has misfolded αS aggregates.

The information obtained by the methods and kits described herein for determining whether there are misfolded αS aggregates in a sample is only an intermediate result or a kind of reference information, and one cannot directly draw a conclusion that an individual has a certain disease based on the result. Therefore, in at least one aspect, what is claimed in this application is not a method for diagnosing a disease.

In another aspect, a method is provided for aiding in diagnosing PD, LBD, MSA, or a spectrum of aspects of each in a subject having a neurological disorder. A neurological disorder is any disorder of the nervous system. Examples of neurological disorders include movement disorders such as PD, autonomic nervous system diseases such as MSA, and neuropsychiatric illnesses such as LBD.

In some aspects, the neurological disorder is a synucleinopathy. Synucleinopathies are neurodegenerative diseases characterized by the abnormal accumulation of aggregates of αS in cells of the nervous system such as neurons, nerve fibers, and glial cells. In some aspects, the synucleinopathy has symptoms associated with PD, LBD, or MSA, including, e.g., impaired cognition, sleep disorders, and gastrointestinal tract dysfunction.

In some aspects, the sample may be taken from a subject exhibiting no clinical signs of PD, LBD, or MSA. In other aspects, the biological sample may be taken from a subject exhibiting clinical signs of PD, MSA, LBD, or any combination thereof. The most recognizable symptom of PD is motor-related dysfunction.

In some aspects, the method includes treating a subject diagnosed as having PD with treatment for PD and/or its symptoms. Deep brain stimulation can be used to reduce motor symptoms associated with PD. Drugs useful for treating the motor symptoms of PD include levodopa, dopamine agonists, and monoamine oxidase B inhibitors. However, additional treatments for PD continue to be developed. See Radhakrishnan D M, Goyal V, Neurol India., 66(Supplement):S26-S35 (2018) and Iarkov et al., Front Aging Neurosci., 12:4 (2020).

Supplemental Diagnostic Tests

In some aspects, the method may further comprise additional tests to confirm the αS-SAA-based indication, for example, to further distinguish the misfolded αS aggregates from a patient indicated by αS-SAA to have PD from the misfolded αS aggregates from a patient indicated by αS-SAA to have MSA or LBD. Examples of additional tests include the use of ligands having a high affinity for one of PD or MSA or LBD misfolded αS aggregates, creating a profile of protease-resistant fragments from the misfolded αS aggregate, and evaluating the structure of the detected misfolded αS aggregate using CD, FTIR, or cryo-ET.

Kits

Another aspect provides a kit for detecting the presence of misfolded αS aggregate in a biological sample. The kit includes a known amount of a monomeric αS substrate; a known amount of an indicator; a buffer composition; optionally one or more beads having a mean diameter from about 1 mm to about 5 mm, from greater than 2.3 mm to about 5 mm, from greater than 3 mm to about 5 mm, about 2.38 mm, about 2.45 mm, or about 3.175 mm; and optionally sarkosyl. The kit also includes sCSF as described herein. The kit may include instructions directing a user to carry out the method of detecting of misfolded αS aggregate as described herein, as well as instructions for testing the competency of the monomeric αS substrate and the αS-SAA buffer, for diluting a biological sample from a peripheral matrix, and for serially diluting biological samples for a semi-quantitative αS-SAA. The kit should also include a package for holding the components of the kit.

A kit generally includes a package with one or more containers holding the reagents, as one or more separate compositions or, optionally, as an admixture where the compatibility of the reagents will allow. The kits may further include buffers, labeling agents, controls, and any other materials necessary for carrying out the detection of misfolded αS aggregate. Kits can also include a tool for obtaining a sample from a subject, such as a swab or other biological fluid collection device.

The kit can also include instructions for using the kit to carry out a method of guiding treatment of a synucleinopathy in a subject. Instructions included in kits can be affixed to packaging material or can be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The kit may include one or more of: a bead distribution apparatus; a multi-well plate including a plurality of wells; a microfluidic plate; a shaking apparatus; an incubating apparatus; and a fluorescence measurement apparatus; included either as one or more of the individual plates or apparatuses, or as a combination device. For example, a shaking microplate reader may be used to perform cycles of incubation and shaking and automatically measure the ThT fluorescence emission during an experiment (e.g., FLUOstar OPTIMA, BMG LABTECH Inc., Cary, N.C. or Buehler Shaker TIMIX 5 shaker).

EXAMPLES

The present invention is illustrated by the following examples. However, the particular examples, materials, amounts, and procedures are to be interpreted broadly in accordance with the scope and spirit of the invention as set forth herein.

Example 1: sCSFs Used as Negative Controls During "Slow Assay" αS-SAA Conditions Control solutions were used as negative controls under "slow assay" αS-SAA conditions. General conditions for the "slow assay" αS-SAA are described in U.S. Pat. No. 10,989,718. The specific αS-SAA conditions used to generate the results herein are as follows:

For negative controls, an incubation mixture was provided in a 96 well plate, the incubation mixture comprising: (1) 1 mg/ml seed-free αS substrate represented by SEQ ID NO: 2; (2) a buffer composition comprising 100 mM PIPES at a pH of 6.5; (3) a salt solution comprising 500 mM NaCl; (4) an indicator comprising 10 μM ThT; and (5) 40 μL of a control solution, for a total volume of 200 μL.

Incubation cycles were performed on the incubation mixture, each incubation cycle comprising: (1) incubating the first incubation mixture for 29 min; and (b) orbitally shaking the incubation mixture for 1 minute at 700 rpm, using an Omega FLUOstar at a constant temperature of 37° C. for 300 total hours, to form an incubated control solution. ThT fluorescence was measured in the plates every 30 minutes at 490 nm after excitation at 440 nm.

Four different control solutions were used:
1. Condition "1B3T": Harvard Apparatus artificial CSF+0.155 mg/mL BSA (1×)+0.042 mg/mL Transferrin (3×)
2. Condition "1.3B": Harvard Apparatus artificial CSF+0.2015 mg/mL BSA (1.3×)
3. Condition "3B1IgG": Harvard Apparatus artificial CSF+0.465 mg/mL BSA (3×)+0.012 mg/mL IgG (1×)
4. Condition "H": Harvard Apparatus artificial CSF Although all of the substrates tested were intended to correspond to SEQ ID NO: 2, the substrates were prepared at different times and some by different expression and/or purification conditions.

The results are shown in Table 1, where "Neg/Total Neg Controls" means the number of trials that showed no substrate self-aggregation compared to the total number of trials. "Pos/Total Neg Controls" means the number of trials that showed substrate self-aggregation compared to the total number of trials.

TABLE 1

| Substrate | Control Solution Composition | Neg/Total Neg Controls | Pos/Total Neg Controls |
|---|---|---|---|
| AMP-6 | 1B3T | 15/15 | 0/15 |
|  |  | 58/60 | 2/60 |
|  |  | 6/6 | 0/6 |

TABLE 1-continued

| Substrate | Control Solution Composition | Neg/Total Neg Controls | Pos/Total Neg Controls |
|---|---|---|---|
|  | 1.3B | 15/15 | 0/15 |
|  |  | 59/60 | 1/60 |
|  | 3B1IgG | 2/2 | 0/2 |
|  |  | 14/15 | 1/15 |
|  | H | 13/15 | 2/15 |
| AMP-12 | 1B3T | 12/12 | 0/12 |
|  |  | 2/2 | 0/2 |
|  |  | 5/6 | 1/6 |
|  | 1.3B | 5/6 | 1/6 |
| AMP-13 | 1B3T | 6/6 | 0/6 |
|  |  | 4/4 | 0/4 |
| AMP-14 | 1B3T | 10/10 | 0/10 |
| AMP-15 | 1B3T | 3/4 | 1/4 |
| AMP-7* | 1B3T | 3/15 | 12/15 |
|  | 1.3B | 3/15 | 12/15 |
| AMP-7A1* | 1B3T | 0/6 | 6/6 |
| AMP-7A2* | 1B3T | 2/6 | 4/6 |
| AMP-11A1* | 1B3T | 0/4 | 4/4 |
| AMP-11A2* | 1B3T | 0/4 | 4/4 |
| AMP-8* | 1B3T | 2/15 | 13/15 |
|  | 1.3B | 0/15 | 15/15 |
| AMP-9* | 1B3T | 9/15 | 6/15 |
|  |  | 1/2 | 1/2 |
|  | 1.3B | 4/15 | 11/15 |
|  |  | 0/2 | 2/2 |
| UGA5-al3* | 1B3T | 0/9 | 9/9 |
|  | 1.3B | 0/15 | 15/15 |
| AMP-10 | 1B3T | 0/2 | 2/2 |
|  | 1.3B | 0/2 | 2/2 |
| AMP-11-1* | 1B3T | 0/8 | 8/8 |
| AMP-11-2* | 1B3T | 0/8 | 8/8 |

*Substrate rejected as inadequate

Figure 3:
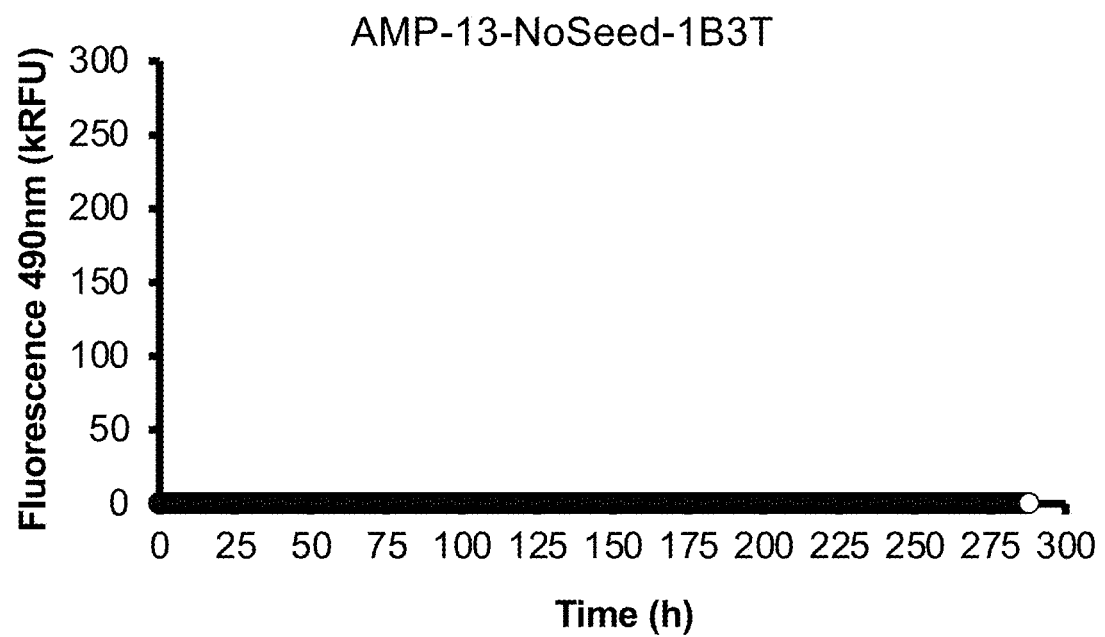
FIG. 3 shows a graph of fluorescence intensity over time for slow αS-SAA of an αS substrate using Harvard Apparatus artificial CSF+0.155 mg/mL BSA+0.042 mg/mL transferrin as a negative control solution.

FIG. 3 shows a graph of fluorescence intensity (in kRFUs) overtime for slow αS-SAA of AMP-13 using 11B3T as the negative control solution.

Figure 4:
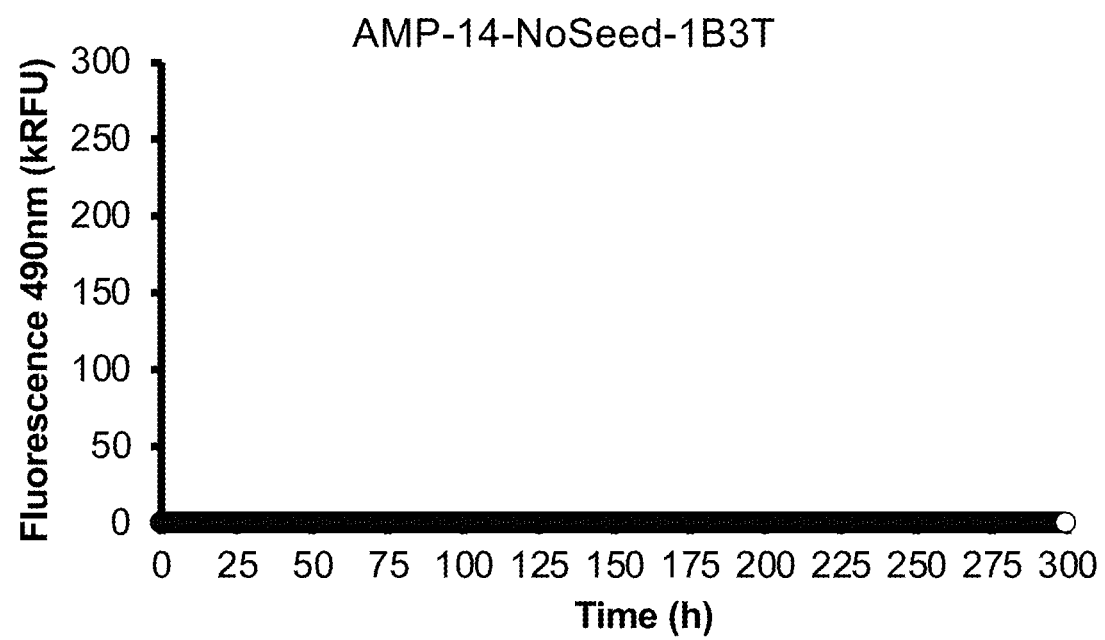
FIG. 4 shows a graph of fluorescence intensity over time for slow αS-SAA of an αS substrate using Harvard Apparatus artificial CSF+0.155 mg/mL BSA+0.042 mg/mL transferrin as a negative control solution.

FIG. 4 shows a graph of fluorescence intensity (in kRFUs) overtime for slow (XS-SAA of AMP-14 using 11B3T as the negative control solution.

Figure 5:
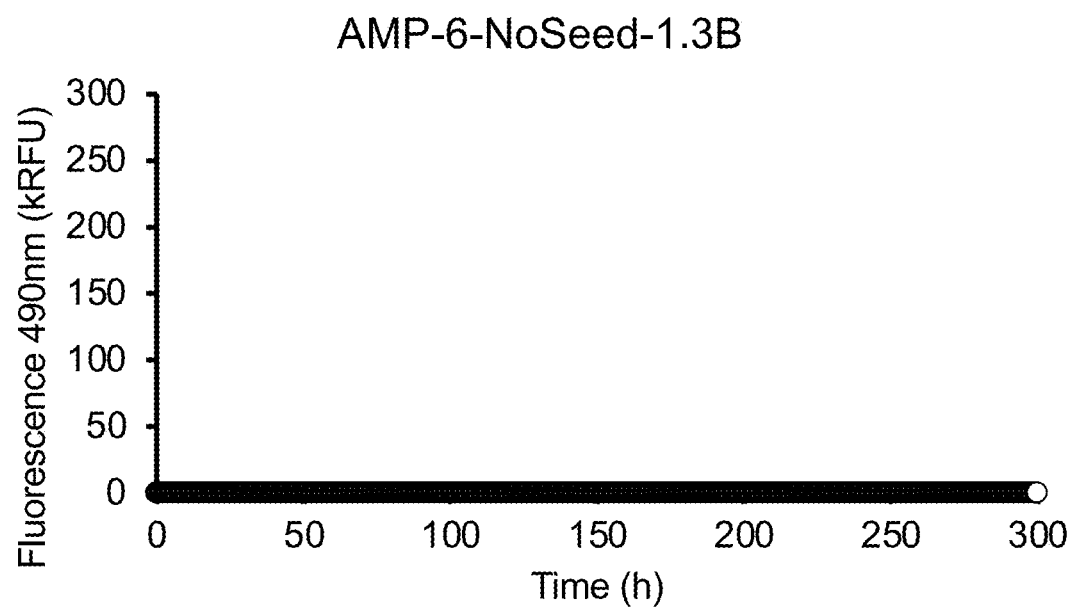
FIG. 5 shows a graph of fluorescence intensity over time for slow αS-SAA of an αS substrate using Harvard Apparatus artificial CSF+0.2015 mg/mL BSA as a negative control solution.

FIG. 5 shows a graph of fluorescence intensity (in kRFUs) overtime for slow (XS-SAA of AMP-6 using 1.3B3 as the negative control solution.

Example 2: sCSFs Used as Positive Controls During "Slow Assay" αS-SAA Conditions Control solutions were used as positive controls during "slow assay" S-SAA conditions. For positive controls, the incubation mixture further comprised 20 fg of synthetic αS aggregates (purchased from Abcam) comprising wild-type human recombinant protein as represented by SEQ ID NO: 1.

The results are shown in Table 2, where "Pos/Total Pos Controls" means the number of trials that show aggregation of substrate with seeds compared to the total number of trials. "Neg/Total Pos Controls" means the number of trials that showed no aggregation of substrate with seeds compared to the total number of trials.

TABLE 2

| Substrate | Control Solution Composition | Pos/Total Pos Controls | Neg/Total Pos Controls |
|---|---|---|---|
| AMP-6 | 1B3T | 14/15 | 1/15 |
|  |  | 60/60 | 0/60 |
|  |  | 40/60 | 20/60 |

TABLE 2-continued

| Substrate | Control Solution Composition | Pos/Total Pos Controls | Neg/Total Pos Controls |
|---|---|---|---|
| | 1.3B | 11/15 | 4/15 |
| | 3B1IgG | 15/15 | 0/15 |
| | H | 5/15 | 10/15 |
| AMP-12 | 1B3T | 8/8 | 0/8 |
| | 1.3B | 6/6 | 0/6 |
| AMP-13 | 1B3T | 4/4 | 4/4 |
| AMP-14 | 1B3T | 8/8 | 8/8 |
| AMP-7* | 1B3T | 12/12 | 0/12 |
| | 1.3B | 12/12 | 0/12 |
| | 1.3B | 34/34 | 0/34 |
| AMP-7A1* | 1B3T | 10/10 | 0/10 |
| AMP-7A2* | 1B3T | 10/10 | 0/10 |
| AMP-11A1* | 1B3T | 4/4 | 0/4 |
| AMP-11A2* | 1B3T | 4/4 | 0/4 |
| AMP-8* | 1B3T | 12/12 | 0/12 |
| | 1.3B | 12/12 | 0/12 |
| AMP-9* | 1B3T | 12/12 | 0/12 |
| | 1.3B | 12/12 | 0/12 |
| UGA5-al3* | 1B3T | 12/12 | 0/12 |
| | 1.3B | 12/12 | 0/12 |
| AMP-10 | 1B3T | 8/8 | 0/8 |
| AMP-11-1* | 1B3T | 4/4 | 4/4 |

*Substrate rejected as inadequate

Figure 6:
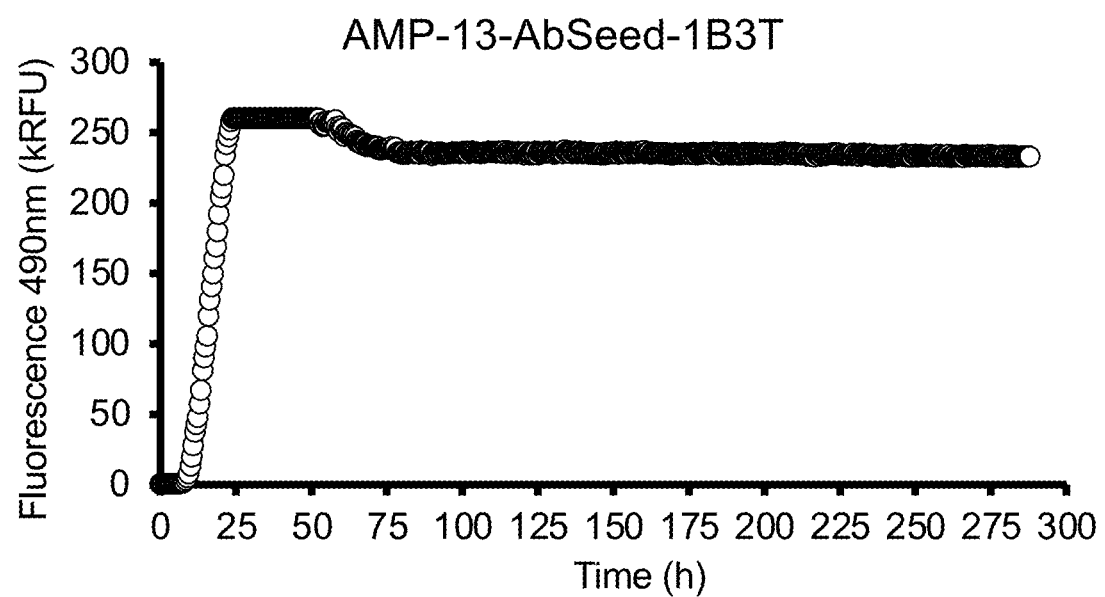
FIG. 6 shows a graph of fluorescence intensity over time for slow αS-SAA of an αS substrate using 20 fg of synthetic seeds in Harvard Apparatus artificial CSF+0.155 mg/mL BSA+0.042 mg/mL transferrin as a positive control solution.

FIG. 6 shows a graph of fluorescence intensity (in kRFUs) overtime for slow (XS-SAA of AMP-13 in the presence of 20 fg of seeds in 11B3T as the positive control solution.

Figure 7:
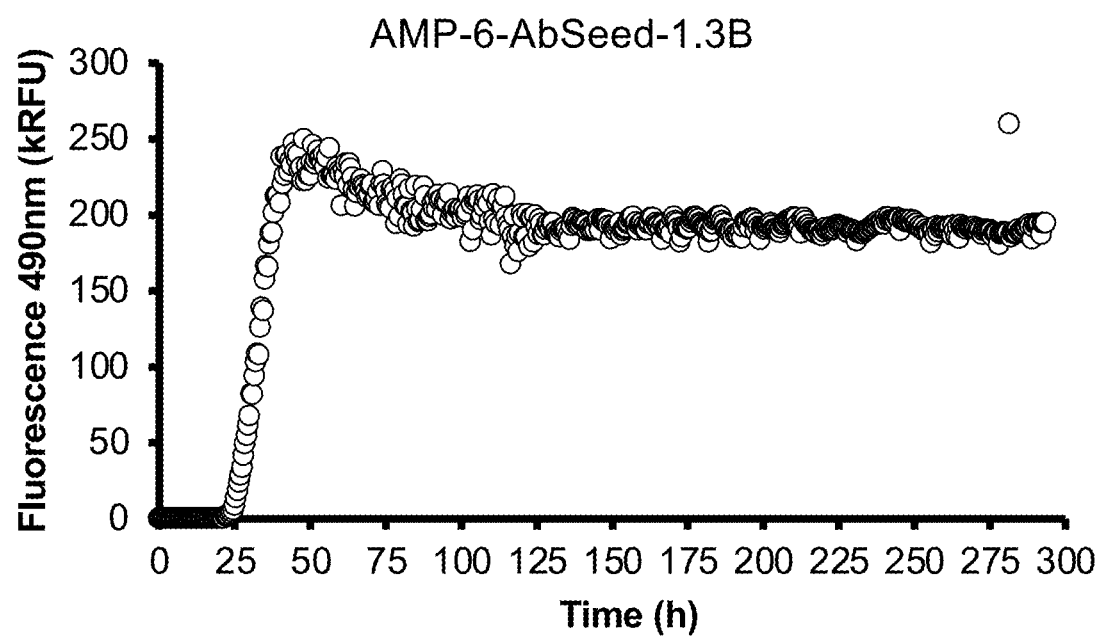
FIG. 7 shows a graph of fluorescence intensity over time for slow αS-SAA of an αS substrate using 20 fg of synthetic seeds in Harvard Apparatus artificial CSF+0.2015 mg/mL BSA as a positive control solution.

FIG. 7 shows a graph of fluorescence intensity (in kRFUs) overtime for slow (XS-SAA of AMP-6 in the presence of 20 fg of seeds in 1.3B3 as the positive control solution.

Example 3: sCSFs Used as Negative Controls During "Fast Assay" αS-SAA Conditions sCSFs were used as negative controls under "fast assay" αS-SAA conditions. General conditions for the "fast assay" αS-SAA are described in U.S. Pat. No. 11,079,396. Specifically, the αS-SAA was conducted using 0.3 mg/ml seed-free αS represented by SEQ ID NO: 2 (which had been properly prepared according to the protocol disclosed in U.S. Pat. No. 11,254,718), orbitally shaken at 800 rpm, in the presence of a 2.38 mm silicon nitride bead.

Figure 8:
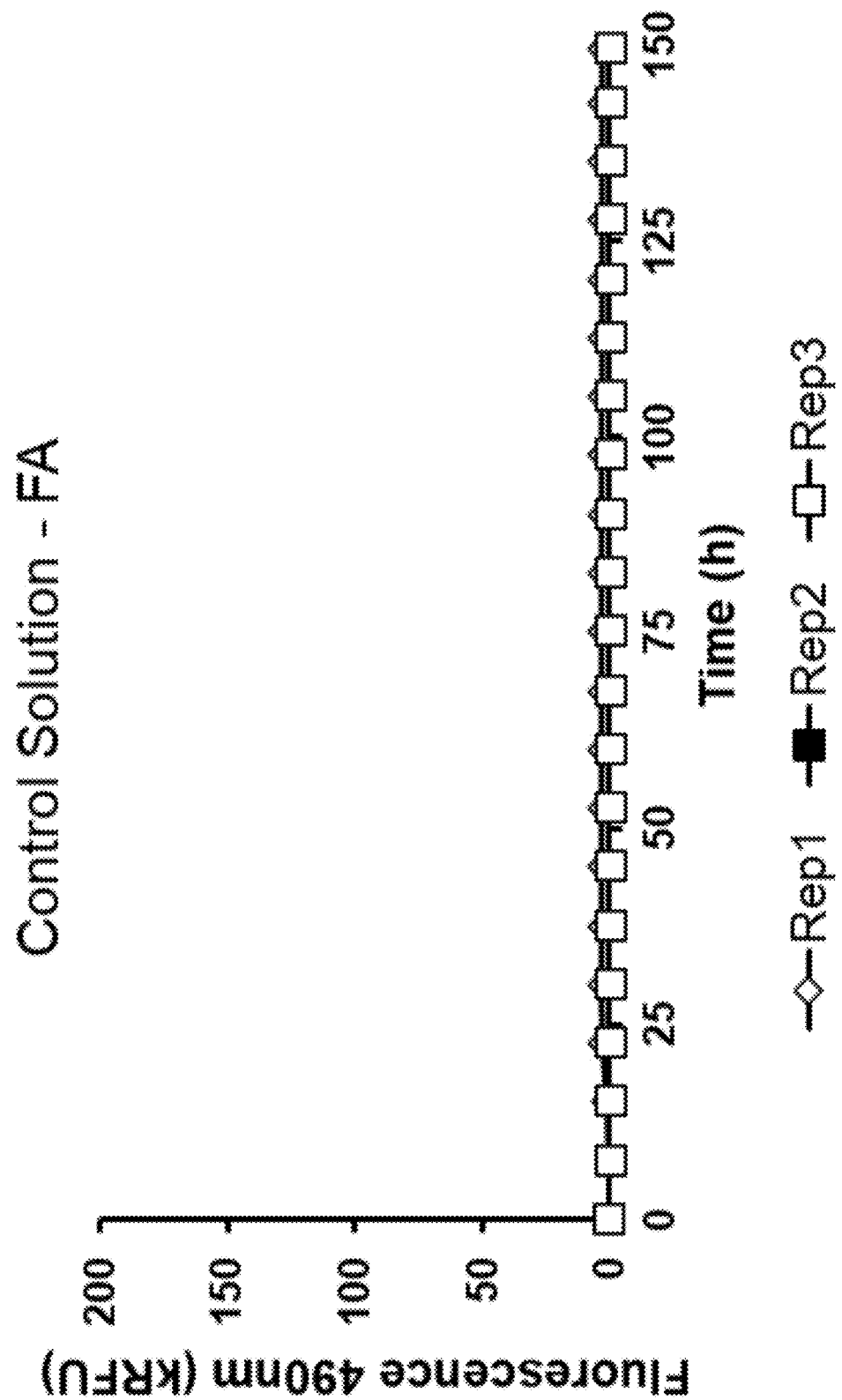
FIG. 8 shows a graph of fluorescence intensity over time for "fast" (that is, using a bead) αS-SAA of a competent αS substrate using 100 mM HEPES, pH 7.5, 75 mM NaCl, 1.5 mg/mL has, and 0.5% sarkosyl as a negative control solution.

FIG. 8 shows a representative graph of fluorescence intensity over time for fast αS-SAA of an αS substrate using 100 mM HEPES, pH 7.5, 75 mM NaCl, 1.5 mg/mL HSA, and 0.5% sarkosyl as a negative control solution. No self-aggregation of the αS substrate is observed in FIG. 8. Out of 96 wells, only 3 (3.1%) showed self-aggregation. In a comparative experiment, the proportion of wells with self-aggregation using healthy human CSF as the control solution produced 5% self-aggregation.

Figure 9:
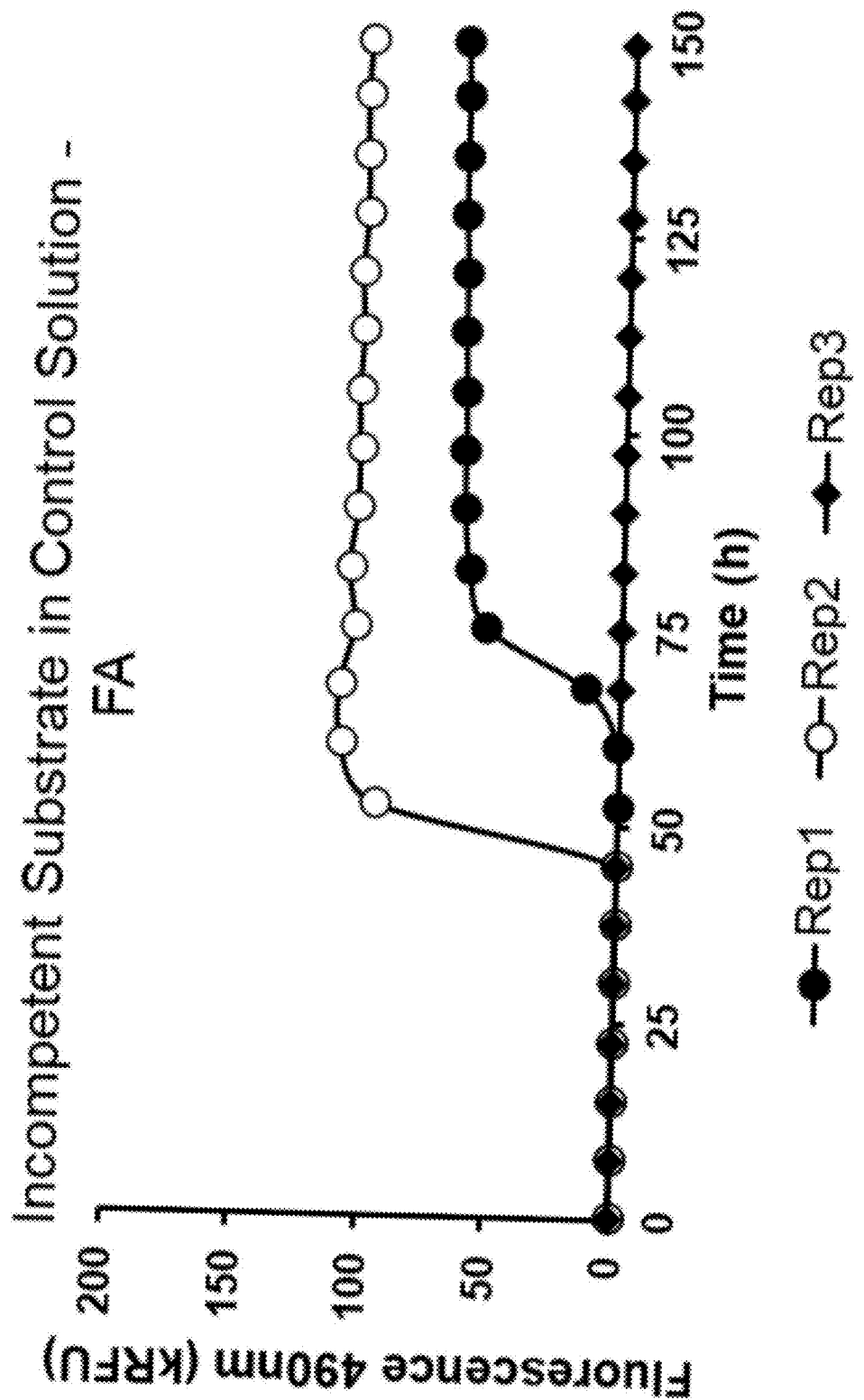
FIG. 9 shows a graph of fluorescence intensity over time for fast αS-SAA of an incompetent αS substrate using 100 mM HEPES, pH 7.5, 75 mM NaCl, 1.5 mg/hasHSA, and 0.5% sarkosyl as a negative control solution.

Example 4: sCSFs for Use in the Screening of Substrate Using "Fast Assay" αS-SAA Conditions The sCSF was used (essentially as a negative control) to screen substrates under "fast assay" αS-SAA conditions. In this experiment, the αS substrate had been purified in a way that deviated from the teaching of U.S. Pat. No. 11,254,718. FIG. 9 shows a graph of fluorescence intensity over time for fast αS-SAA of the incompetent αS substrate using 100 mM HEPES, pH 7.5, 75 mM NaCl, 1.5 mg/mL HSA, and 0.5% sarkosyl as a control solution. As shown in FIG. 9, the αS substrate exhibited self-aggregation.

Example 5: sCSFs Used as Positive Controls During "Fast Assay" αS-SAA Conditions sCSFs were used as positive controls during "fast assay" αS-SAA conditions. For positive controls, the incubation mixture further comprised 20 fg of synthetic αS aggregates (purchased from Abcam) comprising wild-type human recombinant protein as represented by SEQ ID NO: 1.

Figure 10:
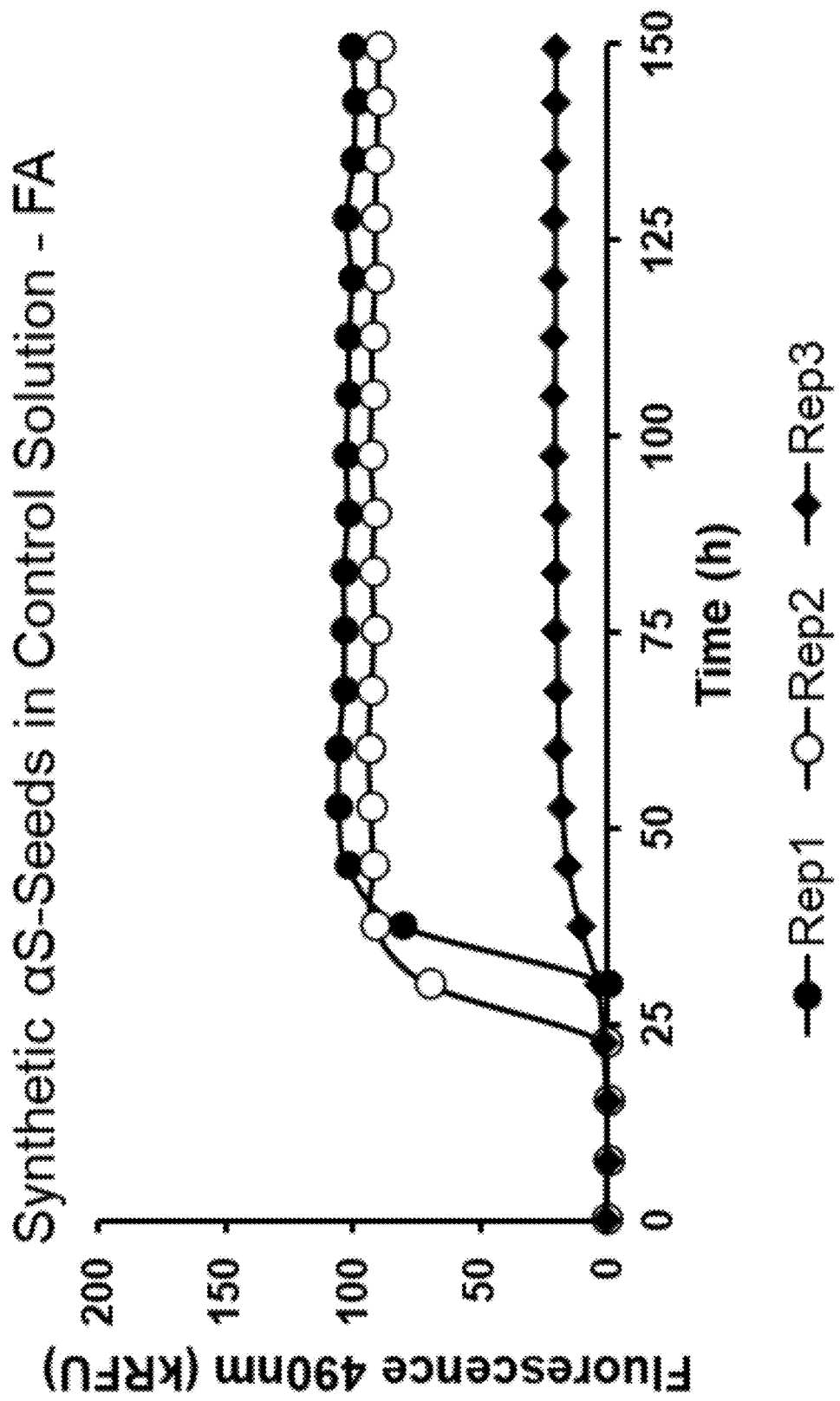
FIG. 10 shows a graph of fluorescence intensity over time for fast αS-SAA of an αS substrate using 20 fg of synthetic seeds in 100 mM HEPES, pH 7.5, 75 mM NaCl, 1.5 hasmL HSA, and 0.5% sarkosyl as a positive control solution.

FIG. 10 shows a graph of fluorescence intensity over time for fast αS-SAA of an αS substrate in the presence of 20 fg of seeds using 100 mM HEPES, pH 7.5, 75 mM NaCl, 1.5 mg/mL HSA, and 0.5% sarkosyl as a positive control solution. FIG. 10 shows the expected aggregation. In fact, 100% of the wells demonstrated the expected aggregation.

Example 6: CSF from HC Used as Diluent

Figure 11:
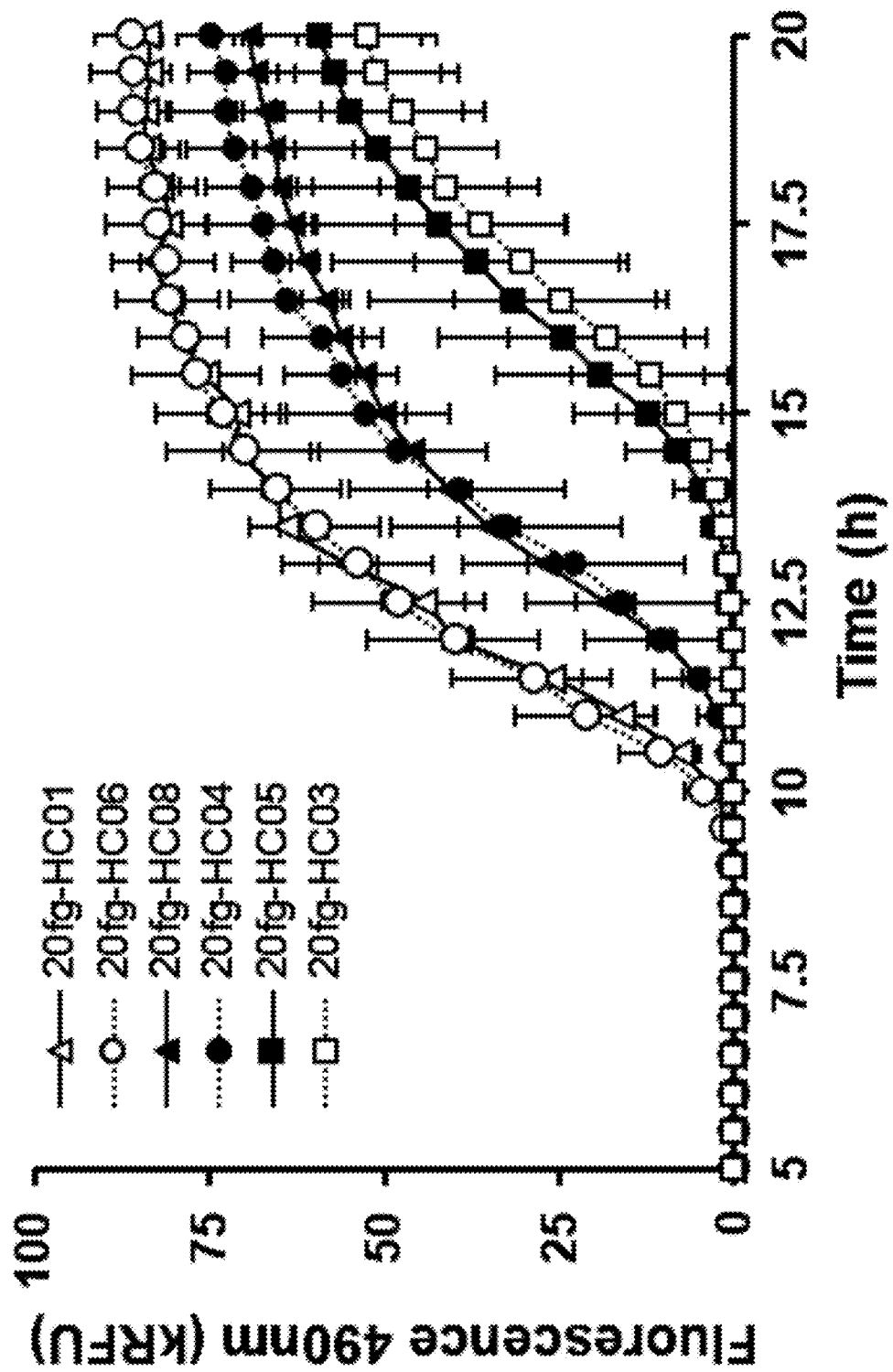
FIG. 11 is a graph showing the variability of aggregation inhibition on αS-SAA when using CSF from different healthy control (HC) donors.

Serial dilutions have been used to determine relative amounts of αS by estimating the dilution at which 50% of the αS-SAA reactions are positive ($SD_{50}$). This estimation relies purely on the number of positive wells, and, thus, kinetic changes due to the particular CSF matrix are not relevant. Positivity of technical replicates decreases when evaluating increasing dilutions of CSF from PD and DLB patients. However, the number of positive wells may change if CSFs from different HC donors are used to dilute. In other words, CSFs from different patients have different effects on aggregation. This variable effect is demonstrable with rec-seeds, which aggregate very reproducibly when spiked in buffer. However, when spiked in CSF from different patients, the aggregation changes based on the CSF sample. See FIG. 11. The effects of each CSF on the rec-seeds were reproducible when the experiment was repeated. Thus, HC-CSF cannot be used as the diluent for serial dilutions, as the titer will change depending on the HC-CSF used. For reproducible titration based on serial dilutions, sCSF as described herein is needed.

Example 7: sCSFs Used as the Diluent in Semi-Quantitative αS-SAA

Serial dilution refers to mixing a volume of a CSF sample containing seeds with another solution (e.g., an sCSF) that does not contain seeds. Serial dilution reduces the concentration of seeds in the mixed sample. An aliquot of the mix is taken for the αS-SAA. The mixed sample is diluted again to generate a higher dilution with an even lower concentration of seeds. This procedure is repeated until the highest desired dilution is reached, i.e., the one that has the lowest concentration of seeds. Here, a 1:3 serial dilution (meaning that each dilution contains 66.6% diluent) up to 1:81 was performed. By analyzing samples this way, a relative number of seeds may be determined, as samples containing more seeds present seeding activity at higher dilutions than samples with a lower concentration of seeds.

For this procedure to be practical, diluent must be plentiful. And for this comparison to be meaningful, all samples must be diluted with the same diluent. Thus, healthy control human CSF is not viable, both in terms of accessibility and in terms of varying protein and other biologic profile across different CSF samples from different patients. The sCSFs described herein allow the commercial and large-scale use of serial dilutions for αS-SAA.

Figure 12A:
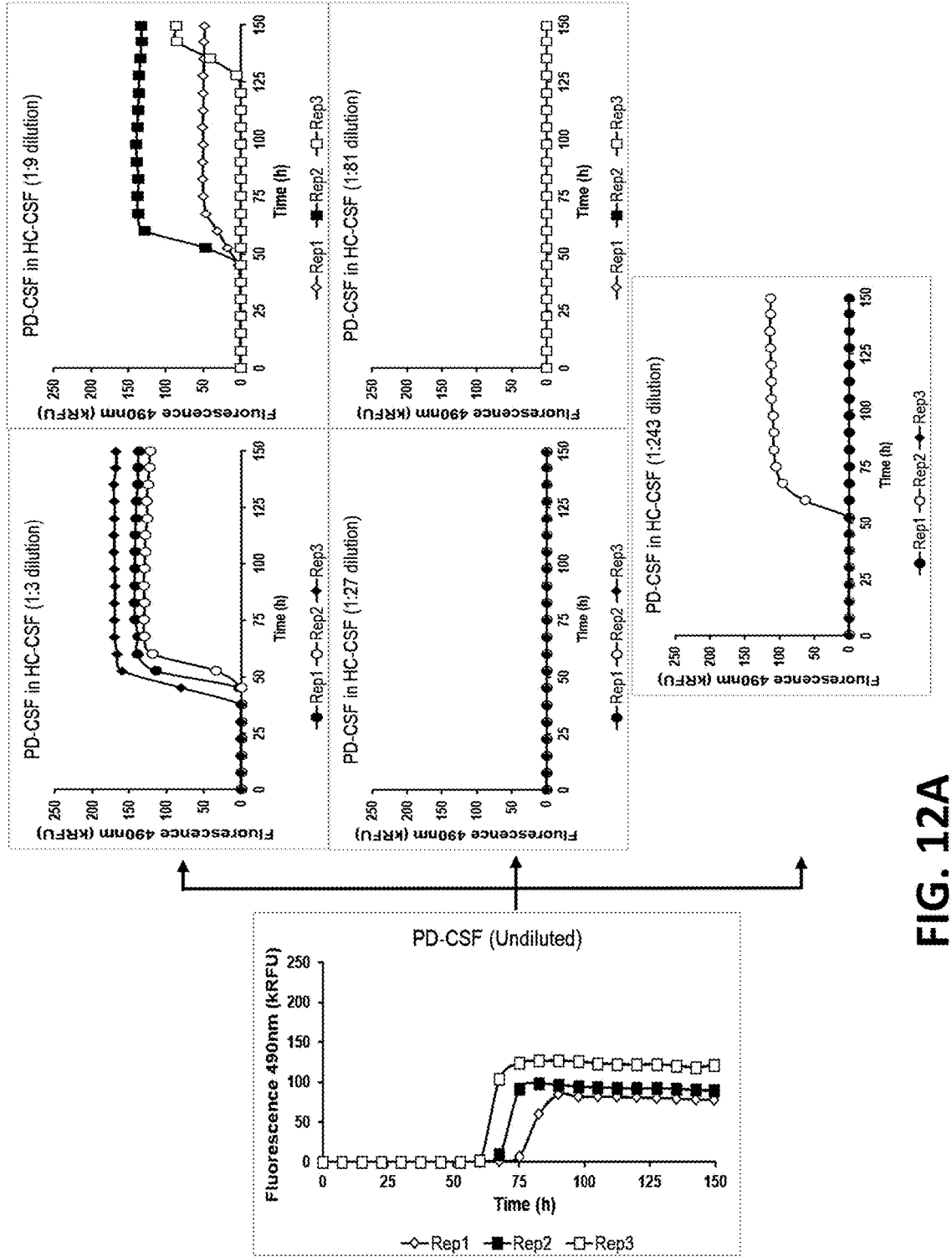
FIG. 12 shows a series of graphs of fluorescence intensity over time during fast αS-SAA conditions of a PD positive sample at serial levels of dilution using 100 mM HEPES, pH 7.5, 75 mM NaCl, 1.5 mg/mL HSA, and 0.5% sarkosyl as the diluent, compared to HC-CSF as diluent and NPH-CSF as diluent.
Figure 12B:
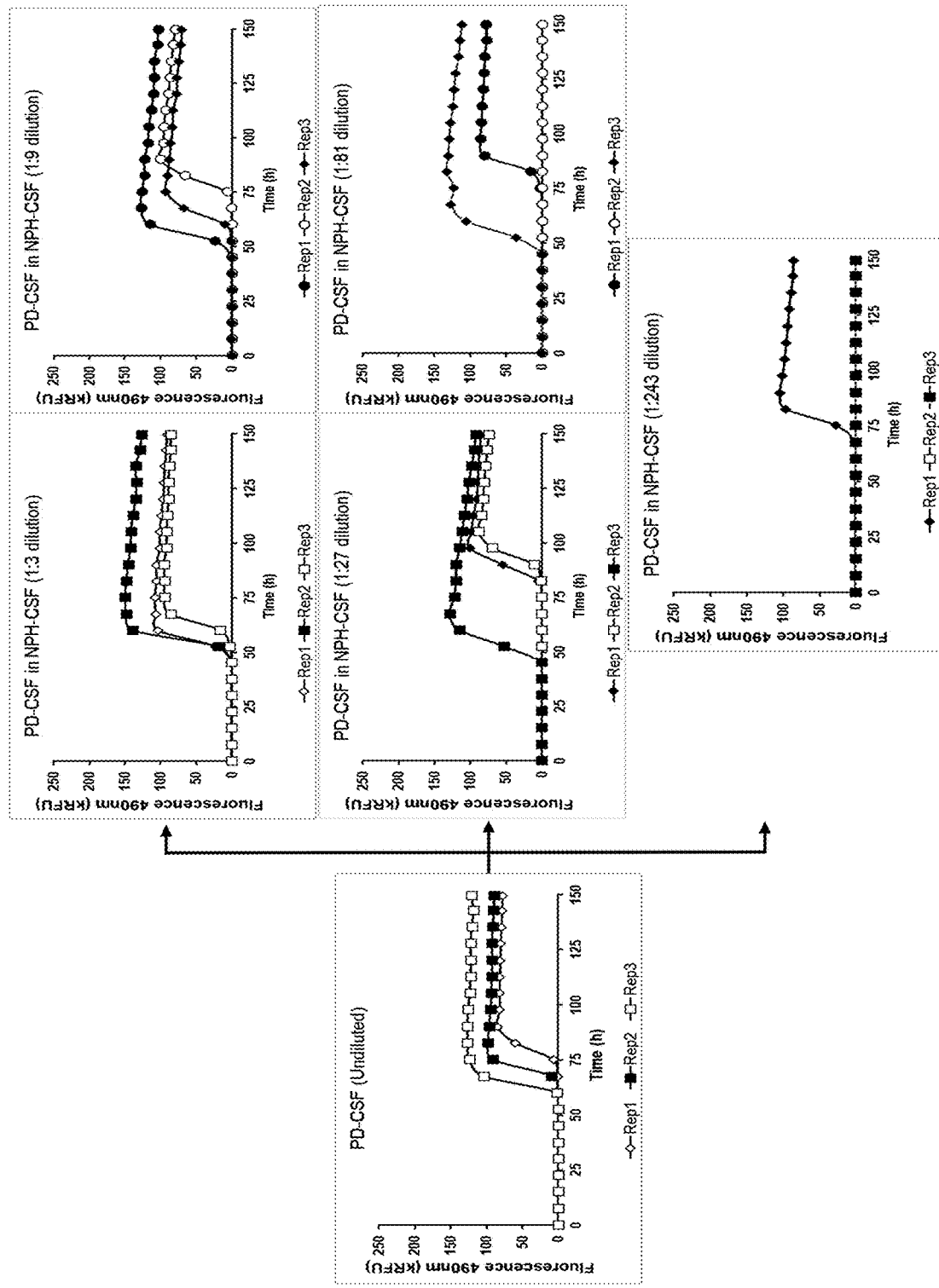
Figure 12C:
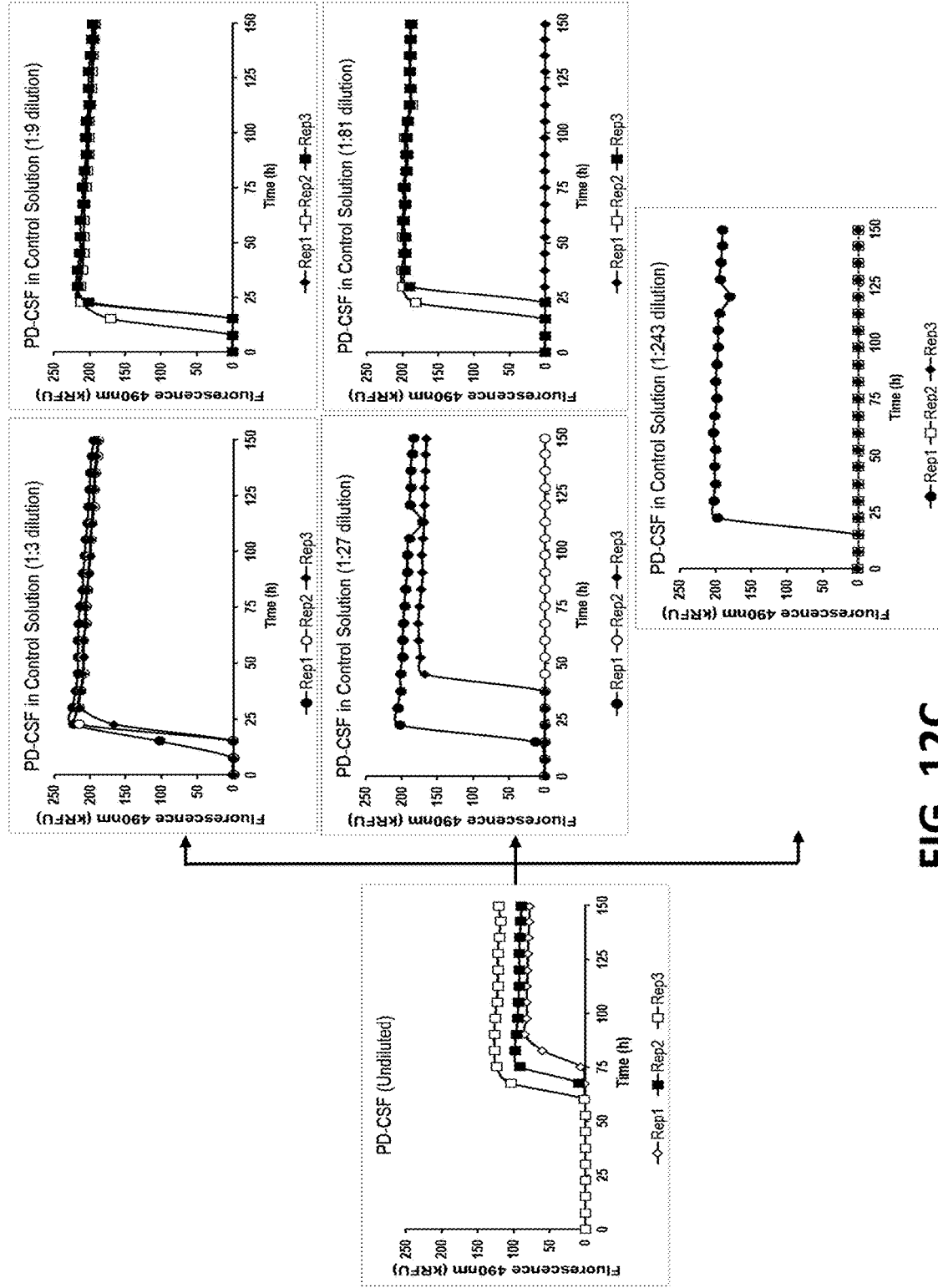

FIG. 12 shows a series of graphs of fluorescence intensity overtime during "fast assay" αS-SAA conditions at serial levels of dilution. FIG. 12 demonstrates that the sCSF consisting essentially of 100 mM HEPES, pH 7.5, 75 mM NaCl, 1.5 mg/mL HSA, and 0.5% sarkosyl replicates the results obtained using CSF from a Normal Pressure Hydrocephalus (NPH) patient, and that the results varied when using CSF from a HC. Both negative NPH and HC are negative in the assay. This emphasizes the need for a stable and reproducible matrix to allow semi-quantification. "SD50," which is the dilution required to have 50% of the wells positive, can be calculated, and the amount of seeds may be estimated. However, even though it is possible to estimate a number of seeds with a standard deviation, the definition of a "seed" is not clear. Therefore, this method will not offer quantification of misfolded αS, but a semi-quantitative alternative to compare seeding activity between samples. Further, the sCSF does not inhibit the amplification as much as HC-CSF, which allows a greater window to differentiate between samples.

Figure 13:
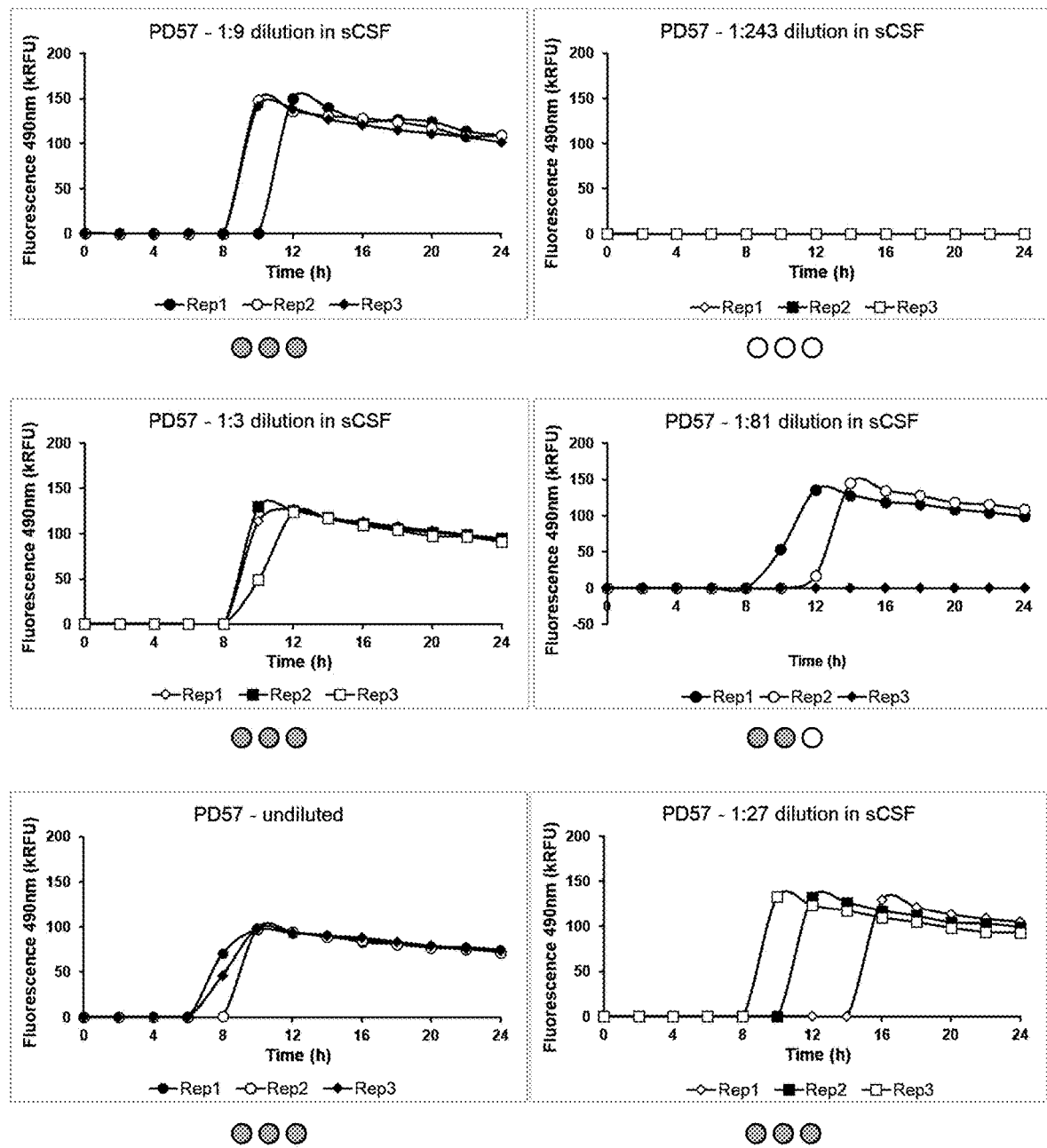
FIG. 13 shows a series of graphs of fluorescence intensity over time during alternative fast αS-SAA conditions of a PD positive sample at serial levels of dilution using 100 mM HEPES, pH 7.5, 75 mM NaCl, and 1.5 mg/mL HSA as the diluent.

FIG. 13 shows a series of graphs of fluorescence intensity over time during alternative "fast assay" αS-SAA conditions (specifically, wherein the assay itself includes sarkosyl, as described in U.S. Pat. No. 11,079,396), of a PD positive sample at serial levels of dilution using 100 mM HEPES, pH 7.5, 75 mM NaCl, and 1.5 mg/mL HSA as the diluent. The three circles underneath each graph represent the three replicates analyzed per dilution. Gray circles represent replicates that presented detectable seed amplification, while white circles represent replicates that presented an absence of detectable seed amplification. This notation is used for FIG. 14, as well.

With further reference to FIG. 14, two CSF samples that have shown strong (2603) and weak (2978) amplification patterns in the fast assay conditions were 3-fold serially diluted in NPH-CSF and sCSF using three substrates and two versions of the fast assay. The $SD_{50}$ was calculated for each sample using the Spearmen-Karber model. Using AMP-A, there was a substantial difference in the seeding activity between these two CSF samples as the estimated number of seeds in 2603 was greater than those in 2978 (67.5>10.8). A similar pattern was observed with AMP50. Estimations of $SD_{50}$ usually present variations in terms of orders of magnitude, and, thus, the results shown in FIG. 14 are very reproducible. Using the same AMP50 substrate, dilutions in sCSF were remarkably similar to the dilutions in NPH-CSF. The alternative fast assay version has demonstrated a lower limit of detection (higher analytical sensitivity), which is also observed here, as higher dilutions of 2603 and 2978 CSF samples presented positive replicates. Overall, all conditions shown in FIG. 14 were able to estimate a higher number of seeds for 2603 than for 2978. (N/T: Not tested. SE: Standard Error.)

Example 8: Semi-Q αS-SAA—Kinetic Normalization

Figure 15:
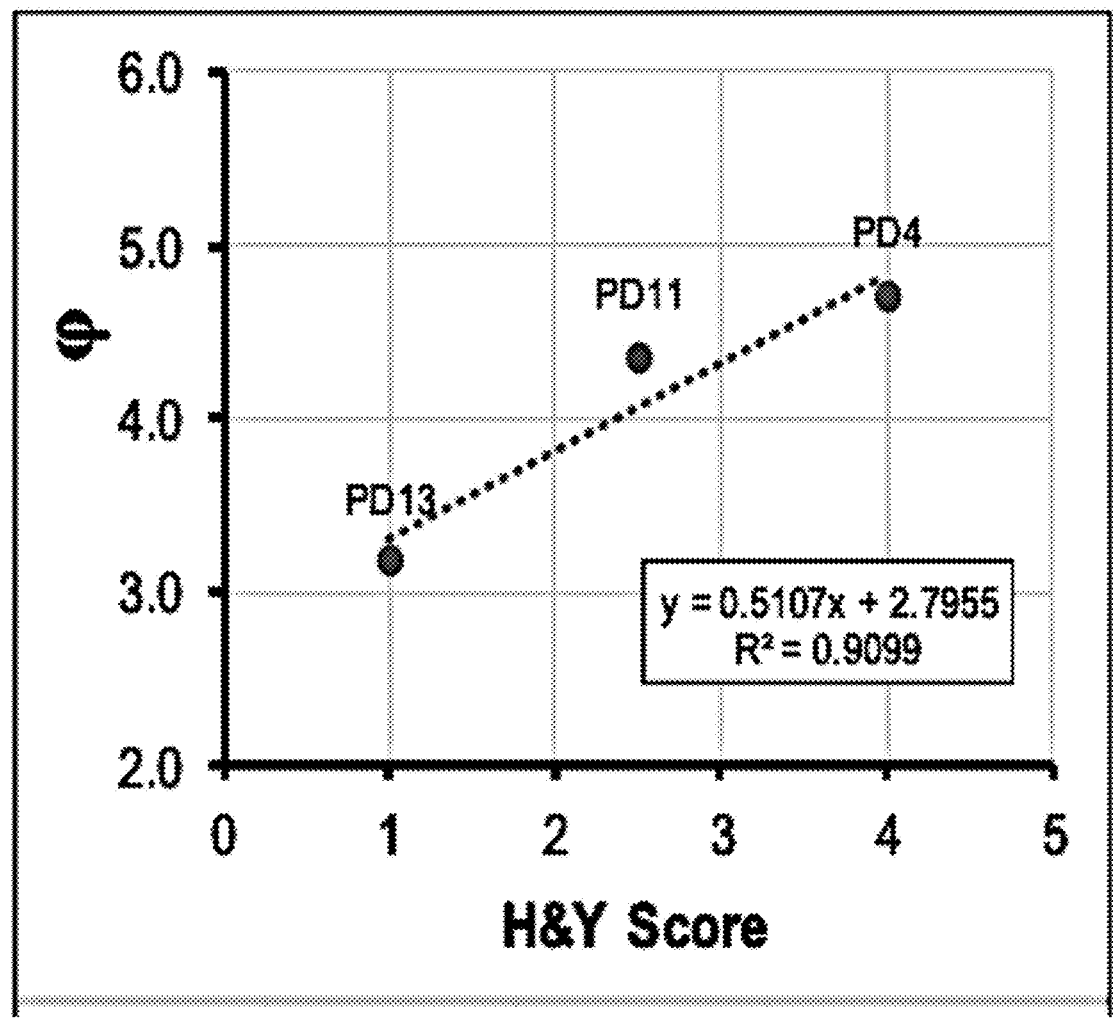
FIG. 15 is a graph showing normalized seeding coefficient (φ) vs. Hoen and Yahr (H&Y) score for three samples from patients diagnosed as having PD.

The $T_{50}$ of rec-seeds changes depending on the CSF donor in a reproducible manner (FIG. 11), revealing inhibitory or amyloidogenic CSF components. Thus, 3 PD-CSF samples were analyzed neat and with spiked rec-seeds. The normalized seeding coefficient ((p) was calculated, and the association with H&Y scores was evaluated. Strikingly, p was strongly associated with H&Y scores. See FIG. 15. Analysis of a larger cohort of samples and additional clinical parameters must be evaluated, including the Unified Parkinson's Disease Rating Scale (UPDRS), the SCales for Outcomes in PArkinson's—Autonomic Dysfuntion (SCOPA-AUT), the Montreal Cognitive Assessment (MoCA) test, and Dopamine Transporter specific binding ratios (DaTscan SBRs), among others.

Example 9: Detection of Misfolded αS Aggregate in Olfactory Mucosa 5.1 Collection and Pre-Processing.

Patients were subjected to local anesthesia (nasal spray with lidocaine) 10 min before the procedure. Through a rigid fiberscope, the olfactory mucosa (between septum and middle turbinate) is identified. Keeping the fiberscope in place, a cotton swab was inserted into the nostril, and once it reached the olfactory mucosa (OM), the wall of the nostril was gently scratched to collect the sample. The swab was removed from the nose and placed in a 15 mL conical tube containing 3 mL of physiological solution (saline buffer). Disposable scissors were used to cut the steam of the swab so that it fit inside the 15 mL conical tube. The tube was vortexed for 1 min. Using disposable tweezers, the swab was transferred to a second 15 mL conical tube with 3 mL of physiological solution (saline buffer) and vortexed for 1 min. With the same disposable tweezers, the swab was transferred to a third 15 mL conical tube with 3 mL of physiological solution and vortexed for 1 min. The swab was discarded. 3 mL from each of the 15 mL tubes (9 mL total) was pooled into a single 15 mL tube, which was centrifuged 800×g for 20 min at 4° C. 8 mL of the supernatant saline solution was discarded. The pellet and 1 mL of saline were stored at −80° C.

5.2 Preprocessing. αS-SAA Sample Preparation.

An OM sample was collected from the pellet using a bacterial inoculation loop that holds ~2 g of sample. Three loops were collected (6 μg) and resuspended in 50 μL of 1×PBS (Sigma, cat #P5493-1L) by extensive vortex and pipetting up-and-down. The final resuspension is aliquoted in three single use aliquots containing 16.7 μL each (2 μg OM sample per aliquot). The sample was snap-frozen and stored at −80° C. until use.

5.3 Sample processing for αS-SAA.

The OM/PBS sample was thawed and 4 μL of sample was pipetted into 76 μL of sCSF (Amprion, cat #52022) to make a 1:20 dilution. A 1:400 (12 ng/40 μL) dilution was prepared by pipetting 24 μL of the 1:20 dilution into 456 μL of sCSF.

5.4 αS-SAA.

Figure 16:
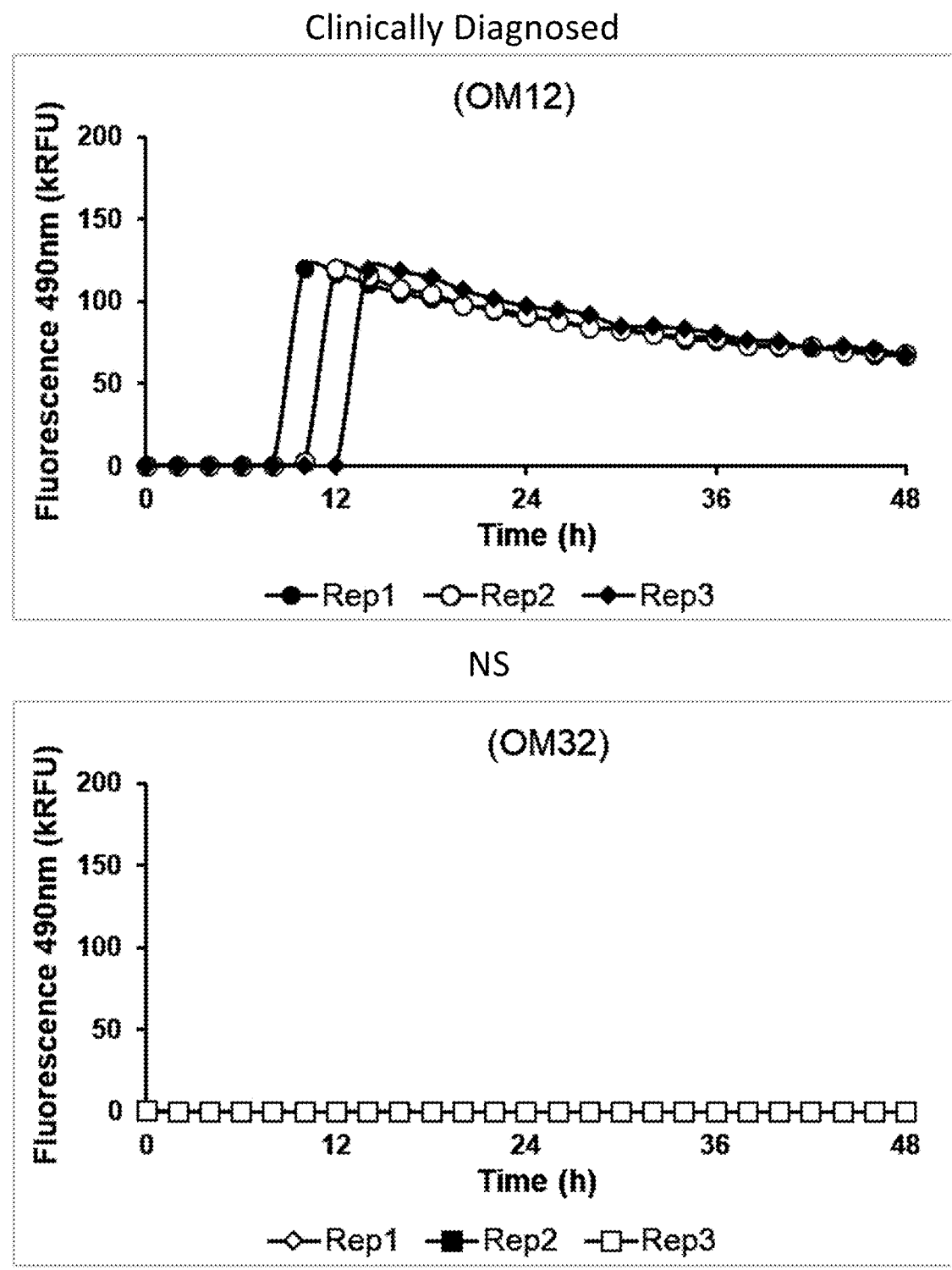
FIG. 16 shows αS-SAA aggregation curves using the monomeric αS substrate corresponding to SEQ ID NO. 2 in the presence of an olfactory mucosa sample from a patient diagnosed as having PD compared to a non-synucleinopathy control. The olfactory mucosa sample was diluted using sCSF as provided herein prior to αS-SAA.

The reaction mixture contained 40 μL OM sample (12 ng and/or 24 ng) and 60 μL of pre-incubation mixture. The pre-incubation mixture included 100 mM PIPES pH 6.5, 500 mM NaCl, 10 μM ThT, 0.1% sarkosyl, and two $Si_3N_4$ beads (⅛", grade 5). Plates are orbitally shaken for 1 min followed by 14 min incubation, for a total 15 min cycle at 42° C. When using a robotic arm associated with the Omega shaker/reader (8 plates at the time), the agitation was set to 600 RPM, while stand-alone Omegas (1 plate at a time) were set to 800 RPM. Fluorescence readings were taken at 440-10 nm (excitation) and 490-10 nm (emission). FIG. 16 shows αS-SAA aggregation curves from a patient diagnosed as having PD compared to a non-synucleinopathy control.

The complete disclosure of all patents, patent applications, and publications, and electronically available material cited herein are incorporated by reference, whether or not the specific citation herein so states. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition, consisting essentially of:
   (A) human serum albumin (HSA);
   (B) aqueous NaCl; and
   (C) (4-(2-hydroxyethyl)-1-piperazineethanesulfonic acid) (HEPES),
   wherein the composition is inert relative to a monomeric alpha-synuclein protein and to a fluorescent protein aggregation indicator.

2. The composition of claim 1, wherein the HSA is present in a concentration of about 1.5 mg/mL.

3. The composition of claim 1, wherein the HSA is present in a concentration of about 15 mg/mL.

4. The composition of claim 1, wherein the HEPES is present in a concentration of about 100 mM.

5. The composition of claim 1, wherein the HEPES maintains a pH of the composition of about 8.

6. The composition of claim 1, wherein the aqueous NaCl has a concentration of about 75 mM.

7. A composition, consisting essentially of:
   (1) about 1.5 mg/mL of human serum albumin;
   (2) (4-(2-hydroxyethyl)-1-piperazineethanesulfonic acid) having a pH of about 8; and
   (3) about 75 mM NaCl; and, optionally,
   (4) about 0.5% sarkosyl,
   wherein the composition is inert relative to a monomeric alpha-synuclein protein and to a fluorescent protein aggregation indicator.

8. The composition of claim 1, the composition consisting of:
   (A) HSA;
   (B) aqueous NaCl; and
   (C) HEPES.

9. A composition, consisting essentially of:
   (A) human serum albumin (HSA);
   (B) aqueous NaCl;
   (C) (4-(2-hydroxyethyl)-1-piperazineethanesulfonic acid) (HEPES); and
   (D) sarkosyl,
   wherein the composition is inert relative to a monomeric alpha-synuclein protein and to a fluorescent protein aggregation indicator.

10. The composition of claim 9, wherein the HSA is present in a concentration of about 1.5 mg/mL.

11. The composition of claim 9, wherein the HEPES is present in a concentration of about 100 mM.

12. The composition of claim 9, wherein the HEPES maintains a pH of the composition of about 8.

13. The composition of claim 9, wherein the aqueous NaCl has a concentration of about 75 mM.

14. The composition of claim 9, wherein the sarkosyl is present in a concentration of about 0.5%.

15. The composition of claim 9, the composition consisting of:
   (A) HSA;
   (B) aqueous NaCl;
   (C) HEPES; and
   (D) sarkosyl.

* * * * *